United States Patent [19]
Williams et al.

[11] Patent Number: 6,107,313
[45] Date of Patent: Aug. 22, 2000

[54] DOPAMINE RECEPTOR ANTAGONISTS

[75] Inventors: John Williams; Karine Lavrador, both of San Diego, Calif.

[73] Assignee: CombiChem, Inc., San Diego, Calif.

[21] Appl. No.: 09/165,505

[22] Filed: Oct. 2, 1998

[51] Int. Cl.[7] .................. C07D 413/04; A61K 31/454
[52] U.S. Cl. .......................... 514/340; 546/269.1
[58] Field of Search ................... 546/269.1; 514/340

[56] References Cited

U.S. PATENT DOCUMENTS

| | | | |
|---|---|---|---|
| 5,262,427 | 11/1993 | Nilson | 514/304 |
| 5,559,128 | 9/1996 | Chakravarty et al. | 514/323 |
| 5,686,463 | 11/1997 | Baker | 514/299 |
| 5,854,261 | 12/1998 | Bosmans | 514/320 |

FOREIGN PATENT DOCUMENTS

| | | | |
|---|---|---|---|
| 0 077 607 A1 | 9/1982 | European Pat. Off. | C07D 405/06 |
| 0 239 309 A2 | 3/1987 | European Pat. Off. | |
| 0 259 621 A2 | 8/1987 | European Pat. Off. | |
| 0 285 032 A1 | 3/1988 | European Pat. Off. | |
| 0 316 718 A2 | 11/1988 | European Pat. Off. | C07D 451/02 |
| 0 323 864 A2 | 1/1989 | European Pat. Off. | C07D 453/02 |
| 0 328 200 A1 | 2/1989 | European Pat. Off. | C07D 453/02 |
| 0 459 568 A2 | 5/1991 | European Pat. Off. | A61K 31/41 |
| 811622 A1 | 6/1997 | European Pat. Off. | |
| 841330 A1 | 11/1997 | European Pat. Off. | |
| 2753970 A1 | 10/1996 | France | |
| 19643037 A1 | 10/1986 | Germany | |
| 2311010 | 3/1997 | United Kingdom | |
| 93/02677 | 2/1993 | WIPO | A61K 31/41 |
| 93/13083 | 7/1993 | WIPO | C07D 271/06 |
| 94/20471 | 9/1994 | WIPO | |
| 94/22839 | 10/1994 | WIPO | |
| 95/07262 | 3/1995 | WIPO | |
| 95/29911 | 11/1995 | WIPO | |
| 95/32965 | 12/1995 | WIPO | C07D 413/04 |
| 96/18630 | 6/1996 | WIPO | |
| 96/25414 | 8/1996 | WIPO | |
| 96/26937 | 9/1996 | WIPO | C07D 413/04 |
| 97/30994 A1 | 2/1997 | WIPO | |
| 9743271 A1 | 5/1997 | WIPO | |
| 9743279 A1 | 5/1997 | WIPO | |
| 9744333 A1 | 5/1997 | WIPO | |
| 9814430 A1 | 9/1997 | WIPO | |
| 99/32486 | 7/1999 | WIPO | C07D 413/04 |

OTHER PUBLICATIONS

Boyfield et al., "Design and Synthesis of 2–Naphthoate Esters as Selective Dopamine $D_4$ Antagonist", *J. Med. Chem.* 39:1946–1948 (1996).

Kulagowski et al., "Dopamine D4 Receptor Antagonist", *Current Phamaceutical Design*, 3:355–366 (1997).

Lahti et al., "Dopamine $D_4$ versus $D_2$ receptor selectivity of dopamine receptor antagonist: possible therapeutic implications", *European Journal of Pharmacology*, 236:483–486 (1983).

Liégeois et al., "Dopamine $D_4$ Receptors: A New Opportunity for Research on Schizophrenia", *Current Medicianal Chemistry*, 5:77–100 (1998).

Rowley et al., "4–Heterocyclylpiperidines as Selective High–Affinity Ligands at the Human Dopamine D4 Receptor", *J. Med. Chem.*, 40:2374–2385 (1997).

Rowley et al., "5–(4–Chlorophenyl)–4–methyl–3–(1–(2–phenylethyl)piperidin–4–yl)isoxazole: A Potent, Selective Antagonist at Human Cloned Dopamine D4 Receptors", 39:1943–1945 (1996).

Seeman et al., "Atypical Neuroleptics Have Low Affinity for Dopamine $D_2$ Receptors or Are Selective for $D_4$ Receptors", *Neuropsychopharm*, 16:2, 93–100 (1997).

Shaikh et al., "Dopamine $D_4$ Receptors, Potential Therapeutic Implications in the Treatment of Schizophrenia", *CNS Drugs*, 8:1–11 (1997).

Andersen, et al., "Oxadiazoles as Bioisosteric Transformations of Carboxylic Functionalities. II", *J. Med. Chem.*, 31:417–425 (1996).

Gupta, et al., "Quantitative Structure–Activity Relationship Studies on Some Nonbenzodiazepine Series of Compounds Acting at the Benzodiazepine Receptor", *Bioorganic & Medicinal Chemical Chemistry*, 6:2213–2218 (1998).

Street, et al., *Synthesis and Biological Activity of 1,2, 4–Oxadiazole Derivatives: Highly Potent and Efficacious Agonists for Cortical Muscarinic Receptors*, *J. Med. Chem.*, 33:10, 2690–2697 (1990).

*Primary Examiner*—Robert Gerstl
*Attorney, Agent, or Firm*—Townsend & Townsend & Crew LLP; Karen B. Dow

[57] ABSTRACT

This invention provides a novel class of oxadiazolyl piperidines which exhibit a high binding affinity for dopamine ligands. The compounds of the invention display selectivity for the dopamine $D_4$ receptor over the dopamine $D_2$ receptor. Preferably, these compounds act as dopamine antagonists, which are useful in the treatment of psychotic disorders.

17 Claims, 13 Drawing Sheets

1   2a: R¹=p-CH₃C₆H₄        3a: R¹=p-CH₃C₆H₄
        2b: R¹=Thienyl           3b: R¹=Thienyl
        2c: R¹=o-CH₃C₆H₄         3b: R¹=o-CH₃C₆H₄

4a: R¹=p-CH₃C₆H₄    5a: R¹=p-CH₃C₆H₄, R²=2,3-dichlorobenzyl
4b: R¹=Thienyl       5b: R¹=Thienyl, R²=4-chlorobenzyl
4c: R¹=o-CH₃C₆H₄     5c: R¹=Thienyl, R²=3-chlorobenzyl
                         5d: R¹=o-CH₃C₆H₄, R²=4-methoxybenzyl

DOPAMINE RECEPTOR ANTAGONISTS

FIELD OF THE INVENTION

This invention relates to a particular class of heteroaromatic compounds. More particularly, the invention is concerned with heteroaromatic piperidine derivatives that are dopamine receptor antagonists.

BACKGROUND OF THE INVENTION

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder that is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London) 350:610 (1991)) and $D_5$ (Sunahara et al., Nature (London) 350:614 (1991)) receptor subtypes have been described.

Notwithstanding their beneficial antipsychotic effects, classical neuroleptic agents such as haloperidol are frequently responsible for eliciting acute extrapyramidal symptoms (e.g., Parkinsonian-like symptoms, tardive dyskensia, dystonia) and neuroendocrine (hormonal) disturbances. These side-effects detract from the clinical desirability of classical neuroleptics, and they are believed to be attributable to $D_2$ receptor blockade in the striatal region of the brain.

It is considered (Van Tol et al., supra; and WO-A-92/10571) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity. The development of dopamine D4 antagonists has been reviewed recently by Kulagowski and Patel, Curr. Pharm. Design 3, 355–366 (1997).

EPA-0285032 discloses a class of phenylpiperidine compounds which are therapeutically active. These compounds are useful in treating pain conditions and they also have neuroleptic properties. Each of the disclosed compounds contains a phenylpiperidine substructure.

EPA-0259621 describes a genus of therapeutically active piperidine compounds which are useful in treating disease related to decreased cognitive function, such as Alzheimers. The compounds are cholinergic agonists which act on the postsynaptic muscarinic receptors in the forebrain and the hippocampus. This disclosure focuses on the interaction of these compounds with muscarinic receptors, not dopamine receptors.

EPA-0077607 describes a class of piperidine derivatives substituted in the 3-position by a substituted phenyl moiety and on the ring nitrogen atom by inter alia an optionally substituted benzofuryl or benzofuryl-alkyl group. Certain of these compounds are stated to be dopamine agonists, whilst others are alleged to be dopamine antagonists. There is no suggestion that the compounds described therein might be potent antagonists of the human dopamine $D_4$ receptor subtype. There is also no teaching that they might have a selective affinity for the dopamine $D_4$ receptor subtype over other dopamine receptor subtypes, and especially the $D_2$ subtype. A similar class of benzo[b]furan compounds is disclosed in WO 95/29911.

EPA-0239309 discloses oxadiazole compounds with a substituent in one of the ring carbons with a non-aromatic azacylic or azabicyclic ring system and substituted on the other ring carbon with a substitutent of low lipophilicity having a Rekker f value of not greater than 1.5. These compounds are useful as muscarinic receptor antagonists.

WP 97/30994 describes oxa and thia-diazolic muscarinic receptor antagonists wherein a benzyl alcohol and a piperidine are substituted on the diazole ring.

Drugs which selectively target and bind to the recently recognized dopamine $D_4$ receptor subclass are promising new treatment modalities for psychotic disorders such as schizophrenia. Drugs which exhibit binding affinities for the $D_4$ receptor subclass which are greater than their binding affinities for the $D_2$ subclass will prove therapeutically useful and cause fewer side effects. The present invention provides a class of such $D_4$ selective agents.

SUMMARY OF THE INVENTION

This invention provides a novel class of heteroaryl piperidines, which interact with dopamine receptors and are, therefore, useful in treating psychotic disorders such as schizophrenia. This class of compounds exhibits selective affinity for the dopamine $D_4$ subtype over the dopamine $D_2$ subtype. As the debilitating side effects caused by currently used antipsychotic medications are thought to be a result of the medication binding to the dopamine $D_2$ receptor, agents which bind selectively to the dopamine $D_4$ are a promising new class of antipsychotic medications which induce minimal or no side-effects.

As such, in a first aspect, the present invention provides a compound having a structure according to Formula I:

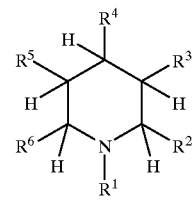

wherein, $R^1$ is a member selected from the group consisting of substituted alkyl, cycloalkyl, aryl, substituted aryl, arylalkyl, substituted arylalkyl, heteroaryl, substituted heteroaryl, heteroarylalkyl and heterocyclicalkyl;

one of $R^2$, $R^3$, $R^4$, $R^5$, and $R^6$ is

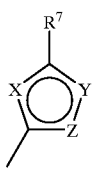

and the other four are each hydrogen;

one of X, Y and Z is oxygen and the other two are nitrogen; and $R^7$ is a member selected from the group consisting of $C_4$–$C_{30}$ alkyl groups, substituted alkyl, cycloalkyl, aryl, substituted aryl, aryl $C_2$–$C_{30}$ alkyl, substituted arylalkyl, heteroaryl, substituted hetereoaryl, heteroarylalkyl, heterocylic and heterocyclic alkyl groups.

Other objects and advantages of the present invention will be apparent to those of skill in the art upon reading the detailed description and examples which follow.

DETAILED DESCRIPTION OF THE INVENTION AND THE PREFERRED EMBODIMENTS

Figure 1:
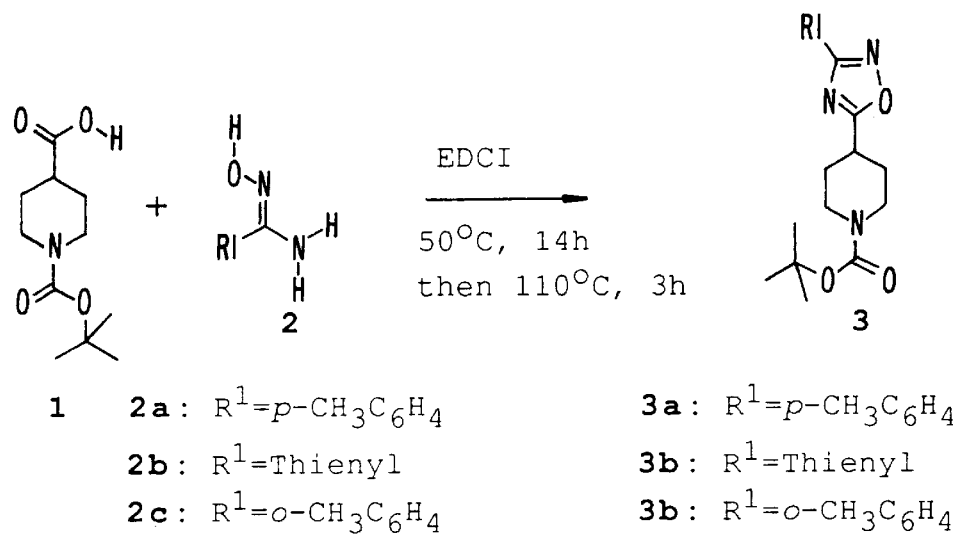
FIG. 1 illustrates a synthetic route useful for producing compounds of the invention.
Figure 1:
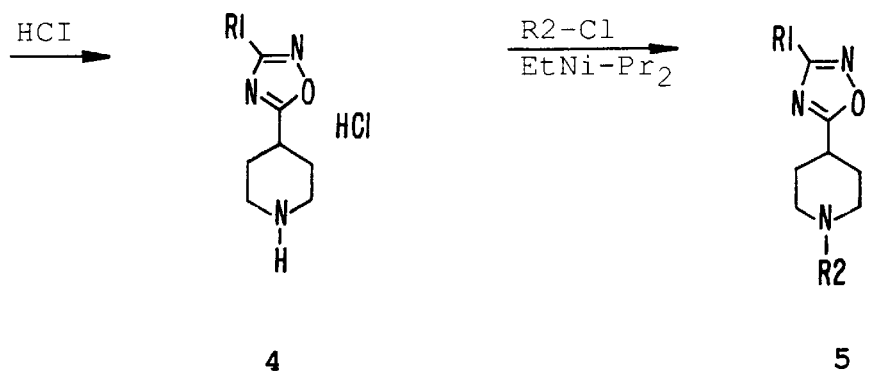
Figure 1:
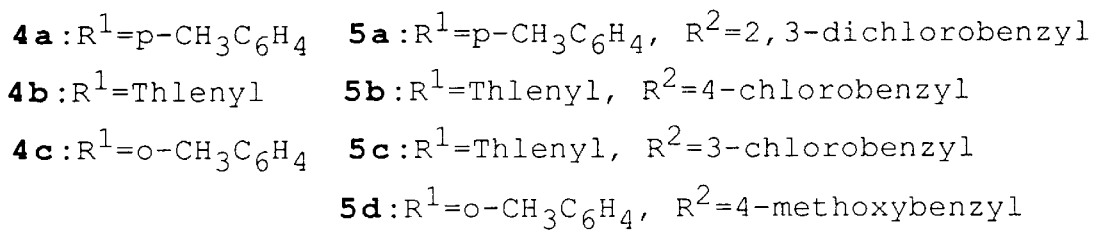
Figure 2:
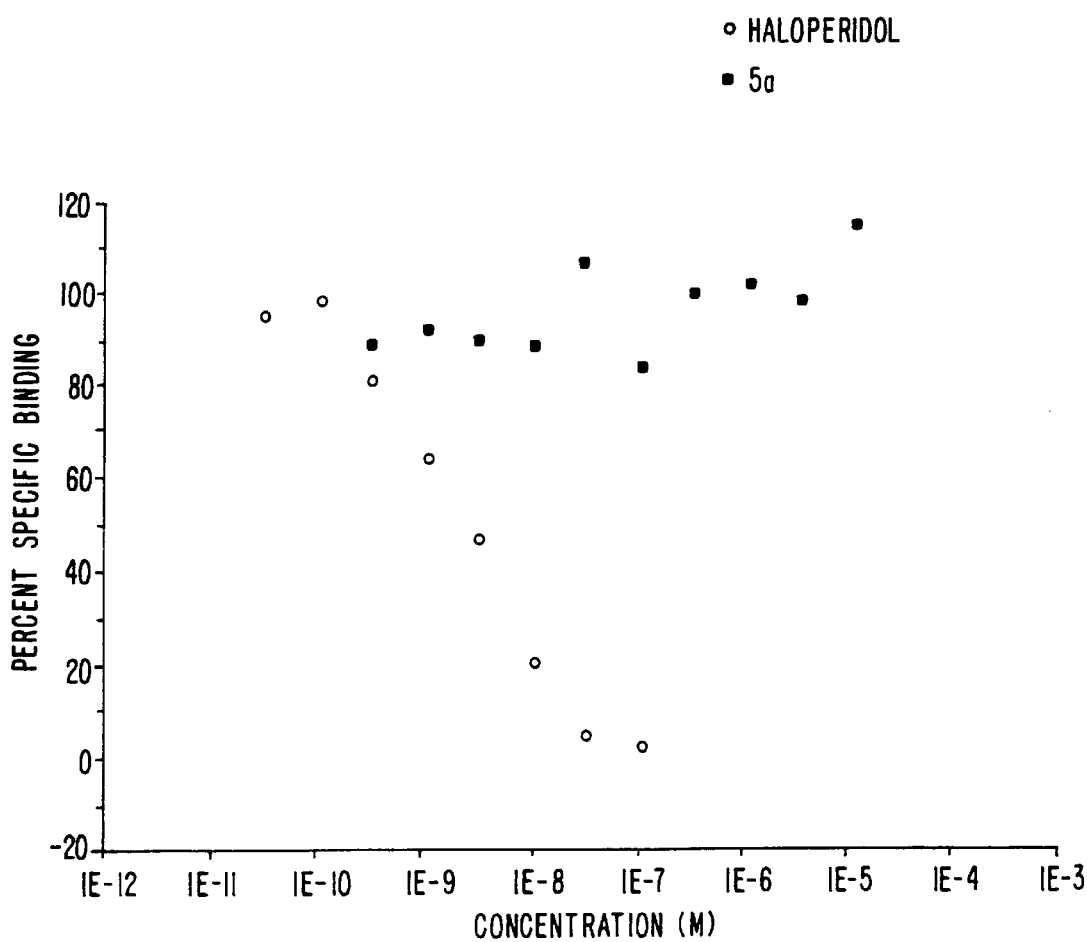
FIG. 2 displays the results of the $IC_{50}/K_i$ determination for compound 5a with the dopamine $D_2$ receptor.
Figure 3:
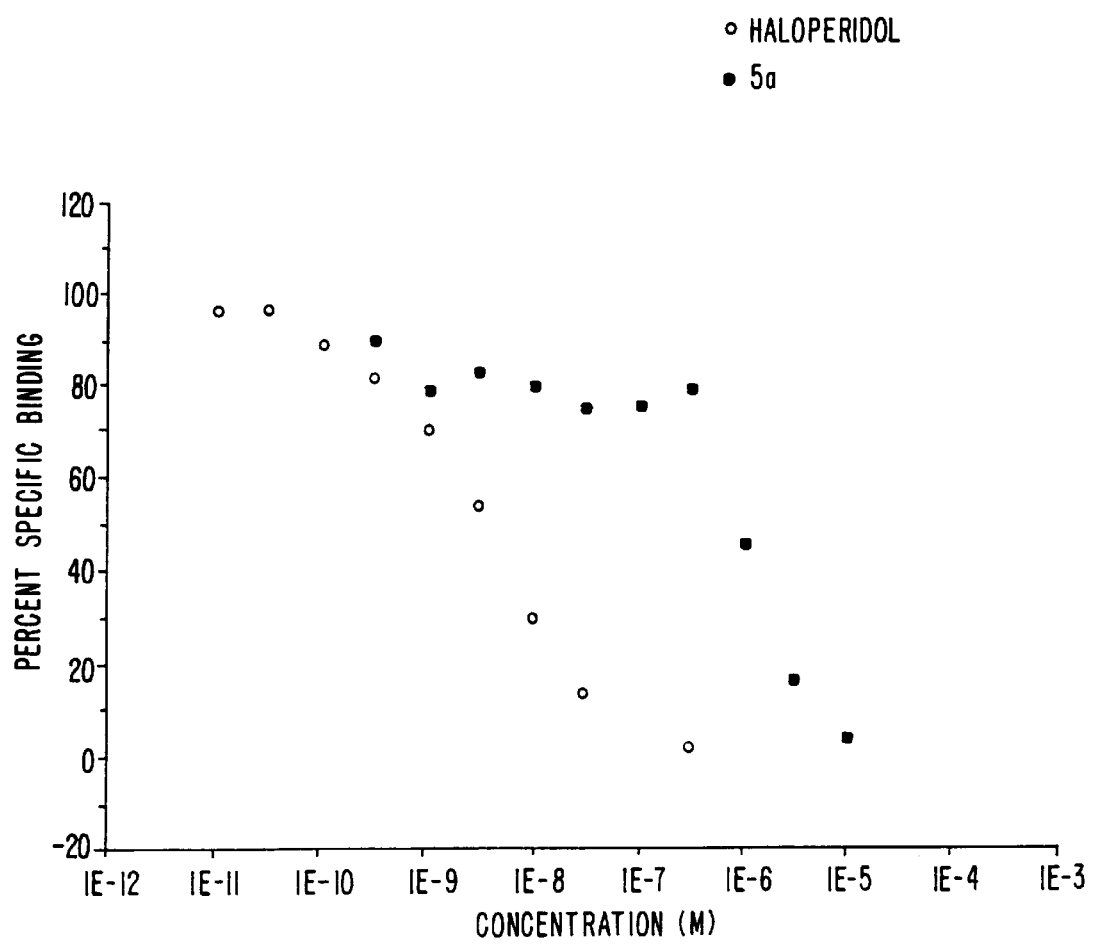
FIG. 3 displays the results of the $IC_{50}/K_i$ determination for compound 5a with the dopamine $D_4$ receptor.
Figure 4:
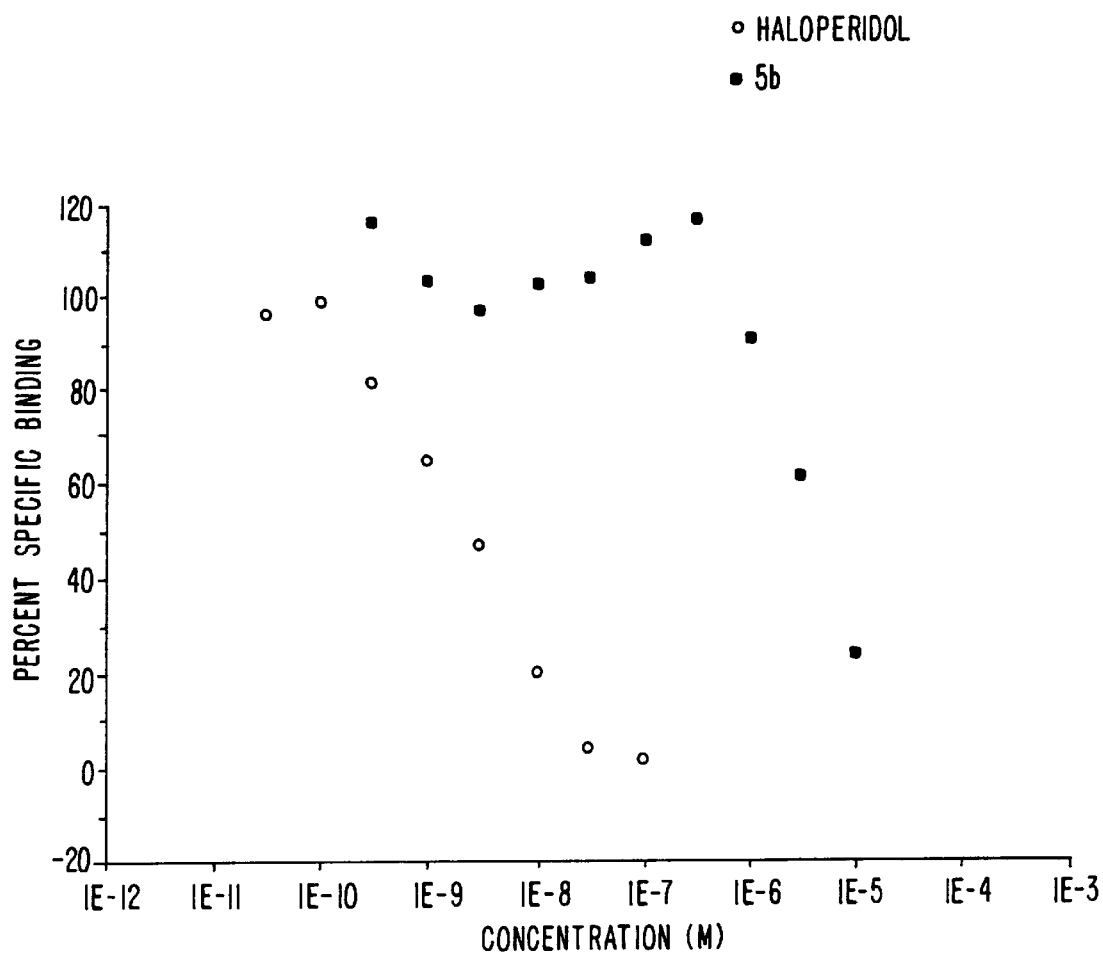
FIG. 4 displays the results of the $IC_{50}/K_i$ determination for compound 5b with the dopamine $D_2$ receptor.
Figure 5:
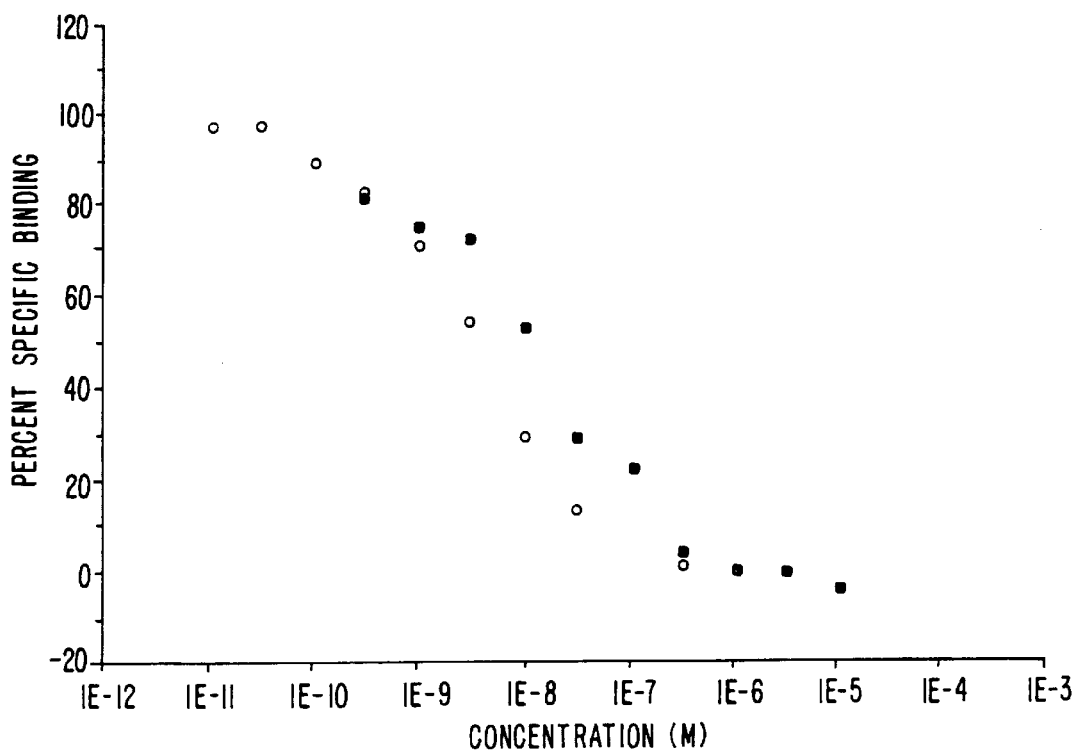
FIG. 5 displays the results of the $IC_{50}/K_i$ determination for compound 5b with the dopamine $D_4$ receptor.
Figure 6:
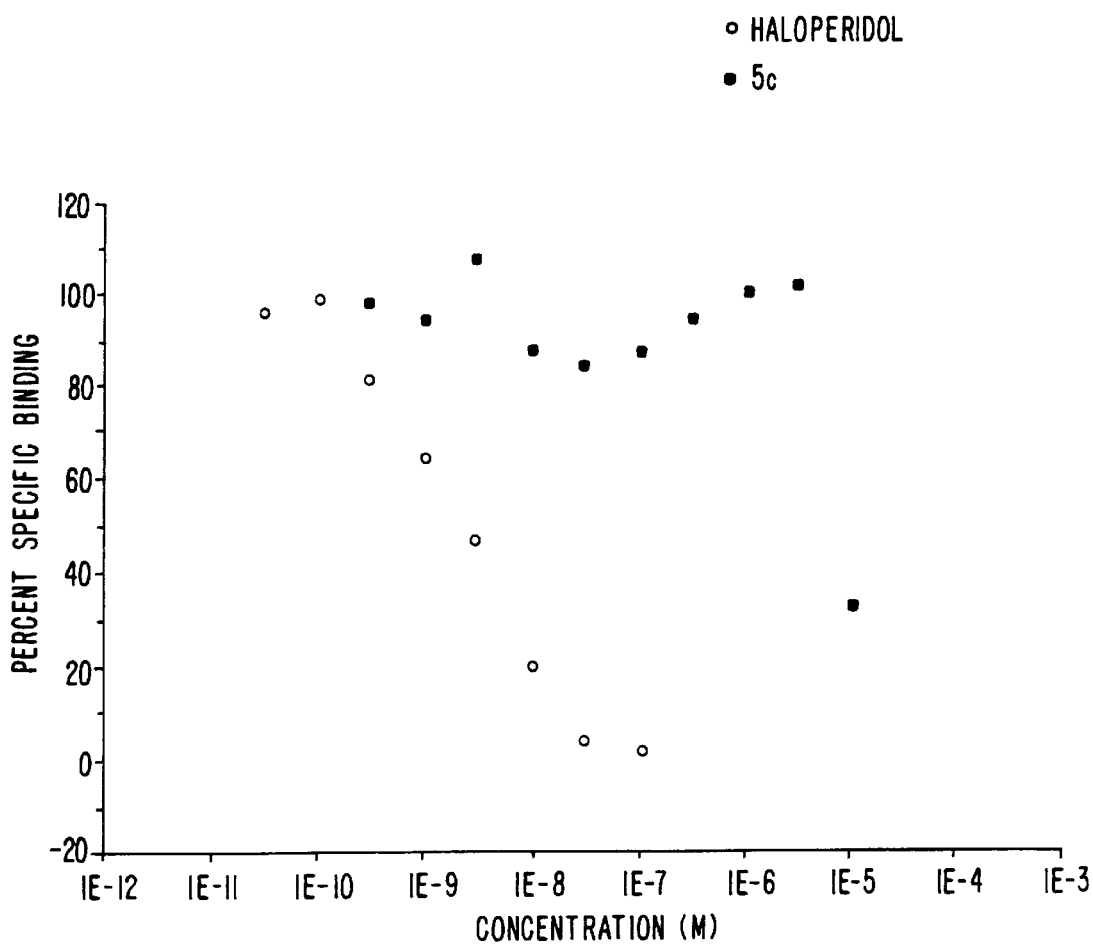
FIG. 6 displays the results of the $IC_{50}/K_i$ determination for compound 5c with the dopamine $D_2$ receptor.
Figure 7:
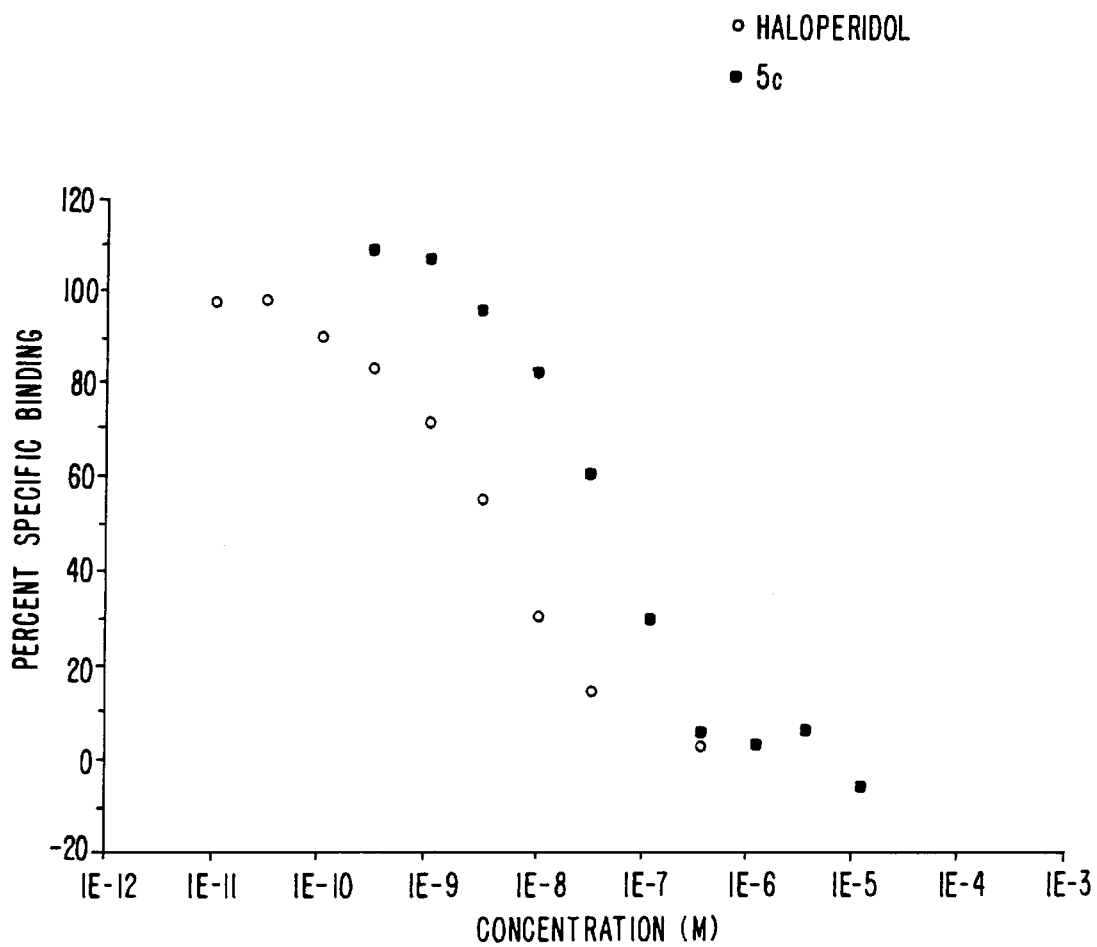
FIG. 7 displays the results of the $IC_{50}/K_i$ determination for compound 5c with the dopamine $D_4$ receptor.
Figure 8:
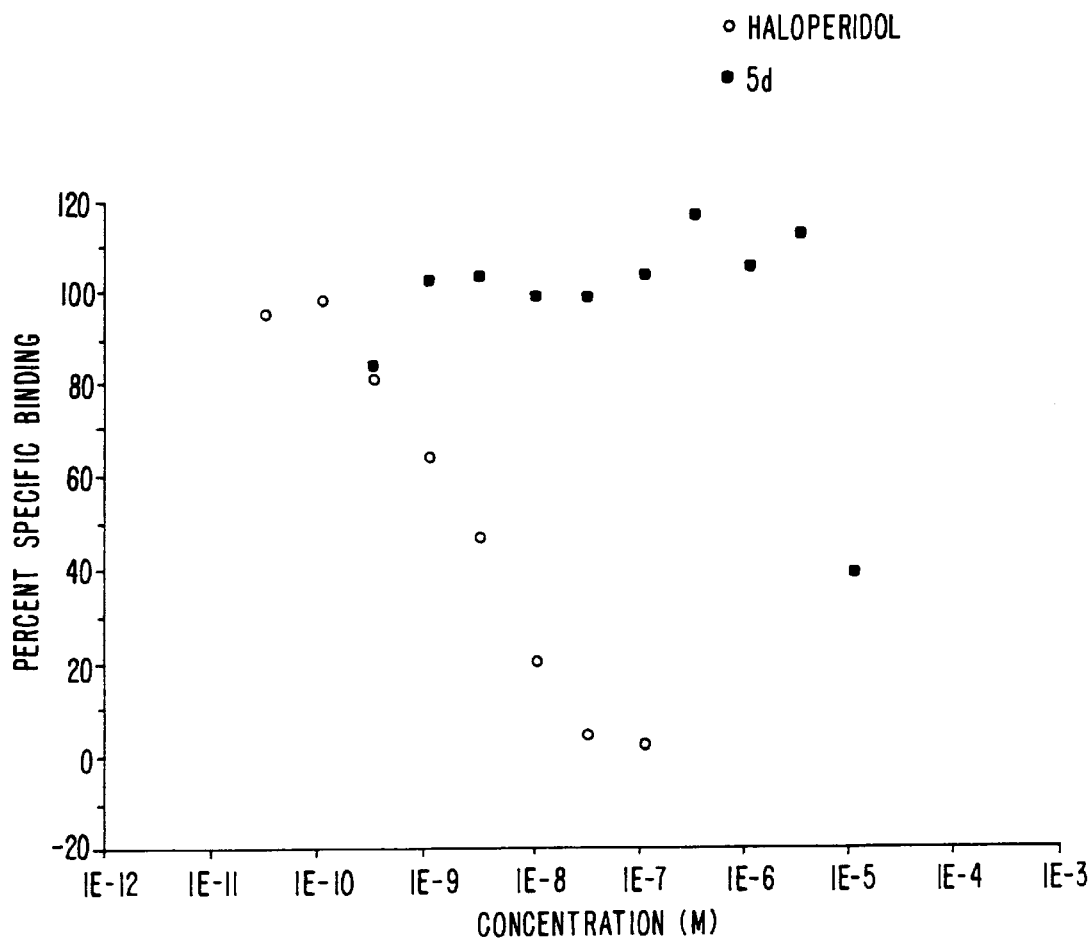
FIG. 8 displays the results of the $IC_{50}/K_i$ determination for compound 5d with the dopamine $D_2$ receptor.
Figure 9:
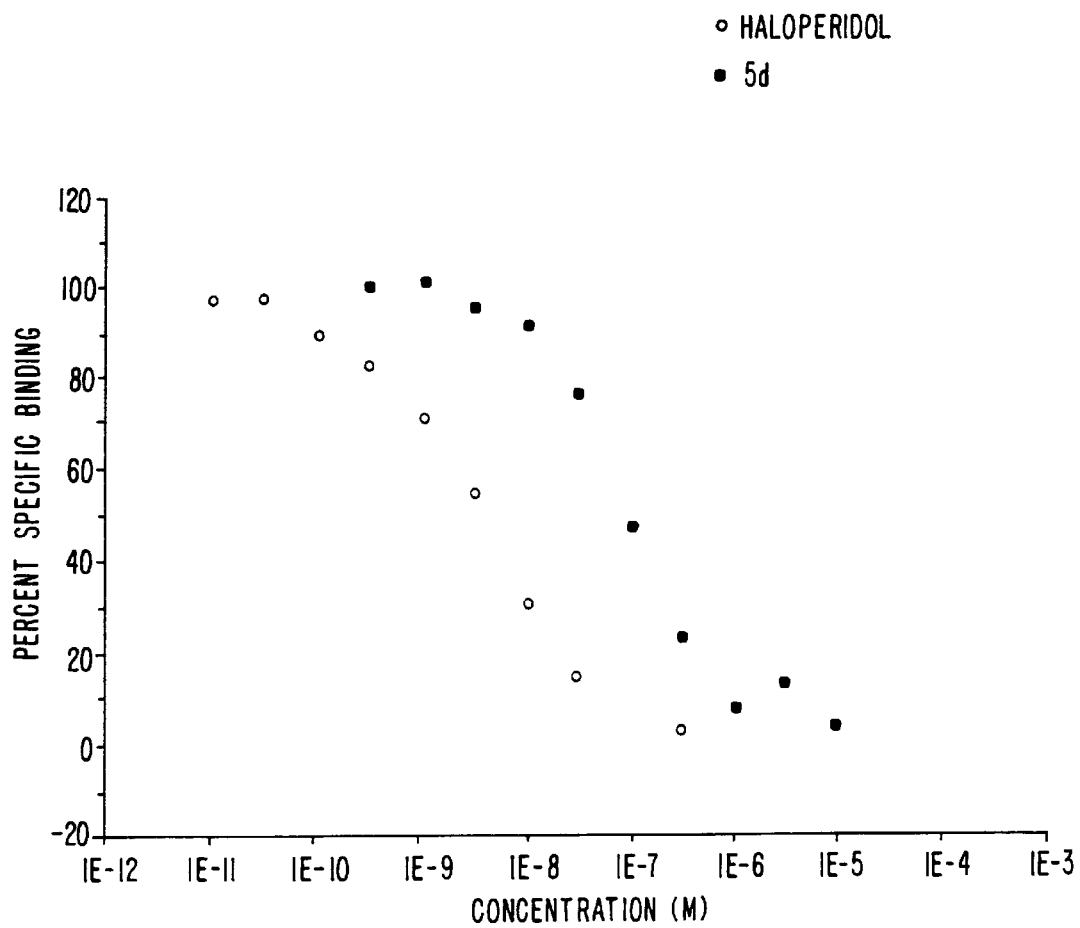
FIG. 9 displays the results of the $IC_{50}/K_i$ determination for compound 5d with the dopamine $D_4$ receptor.
Figure 10:
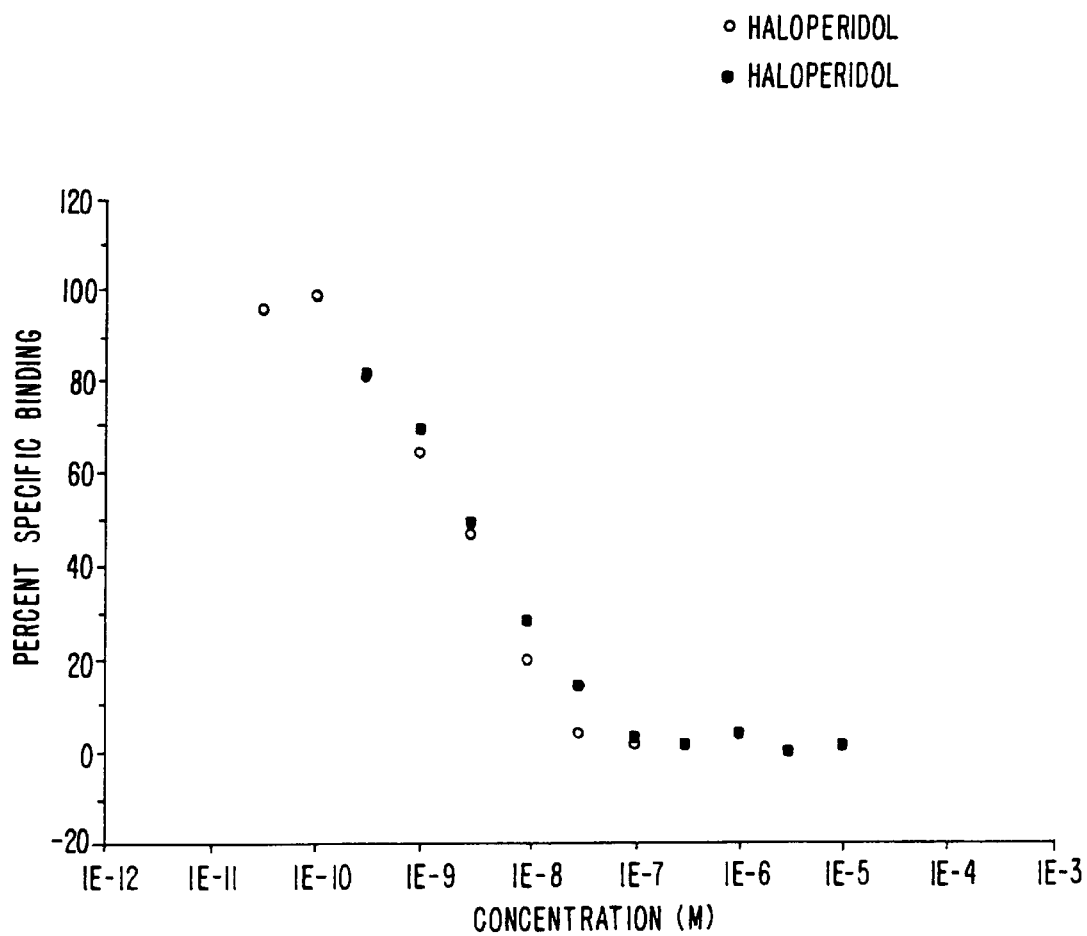
FIG. 10 displays the results of the $IC_{50}/K_i$ determination for haloperidol with the dopamine $D_2$ receptor.
Figure 11:
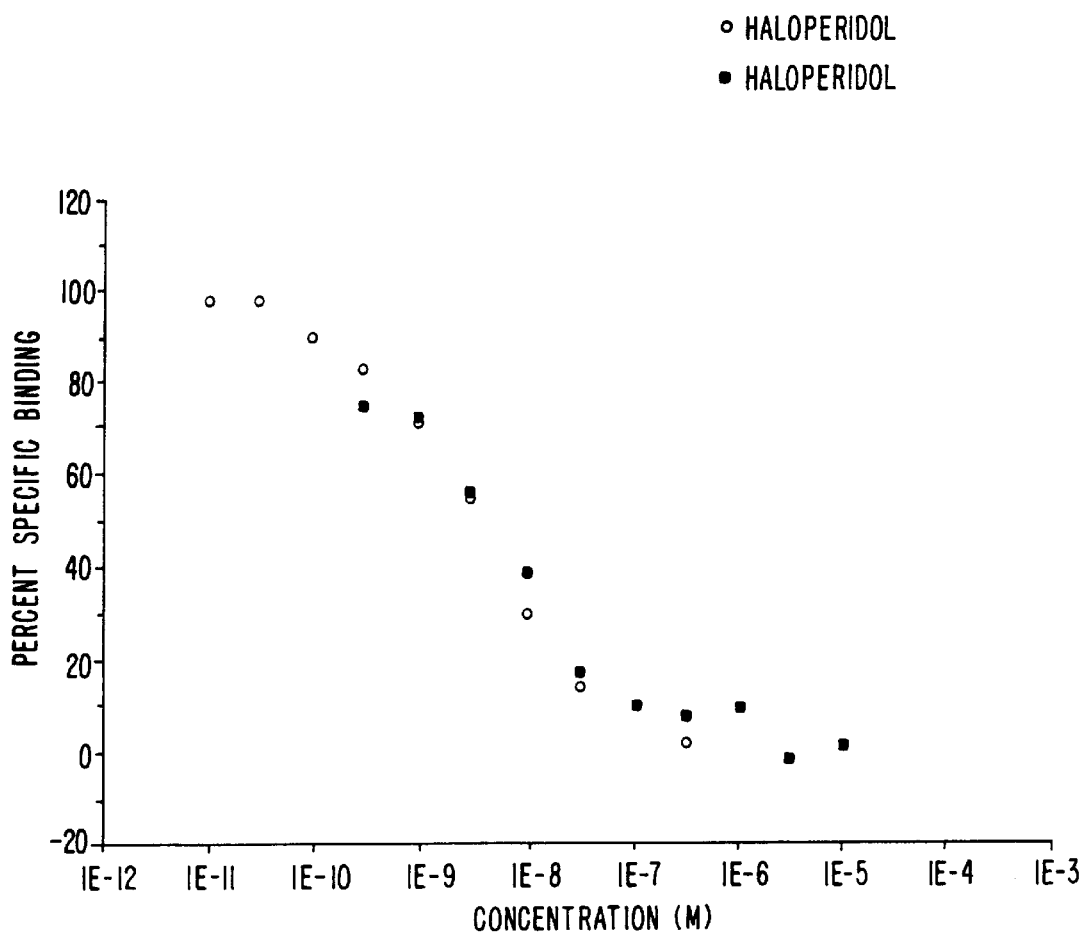
FIG. 11 displays the results of the $IC_{50}/K_i$ determination for haloperidol with the dopamine $D_4$ receptor.
Figure 12:
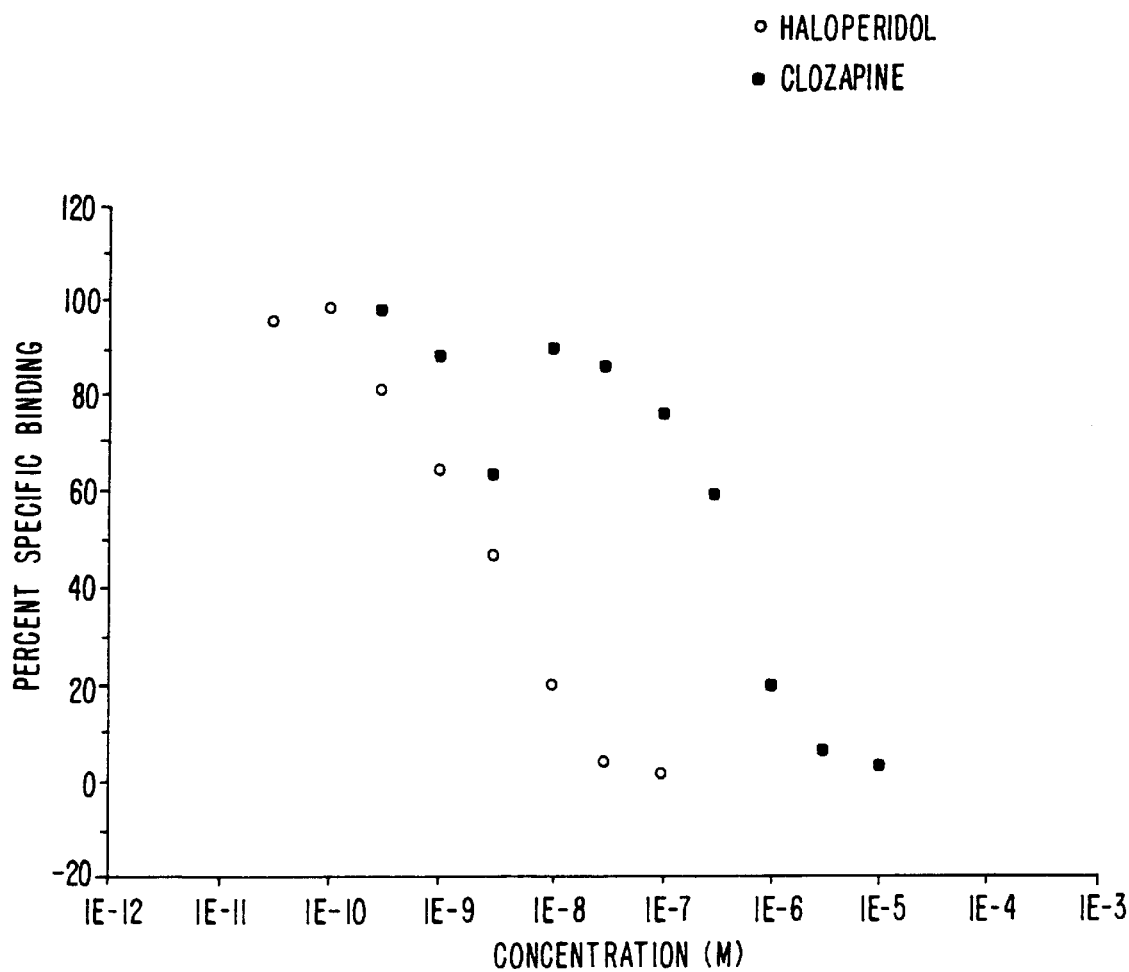
FIG. 12 displays the results of the $IC_{50}/K_i$ determination for clozapine with the dopamine $D_2$ receptor.
Figure 13:
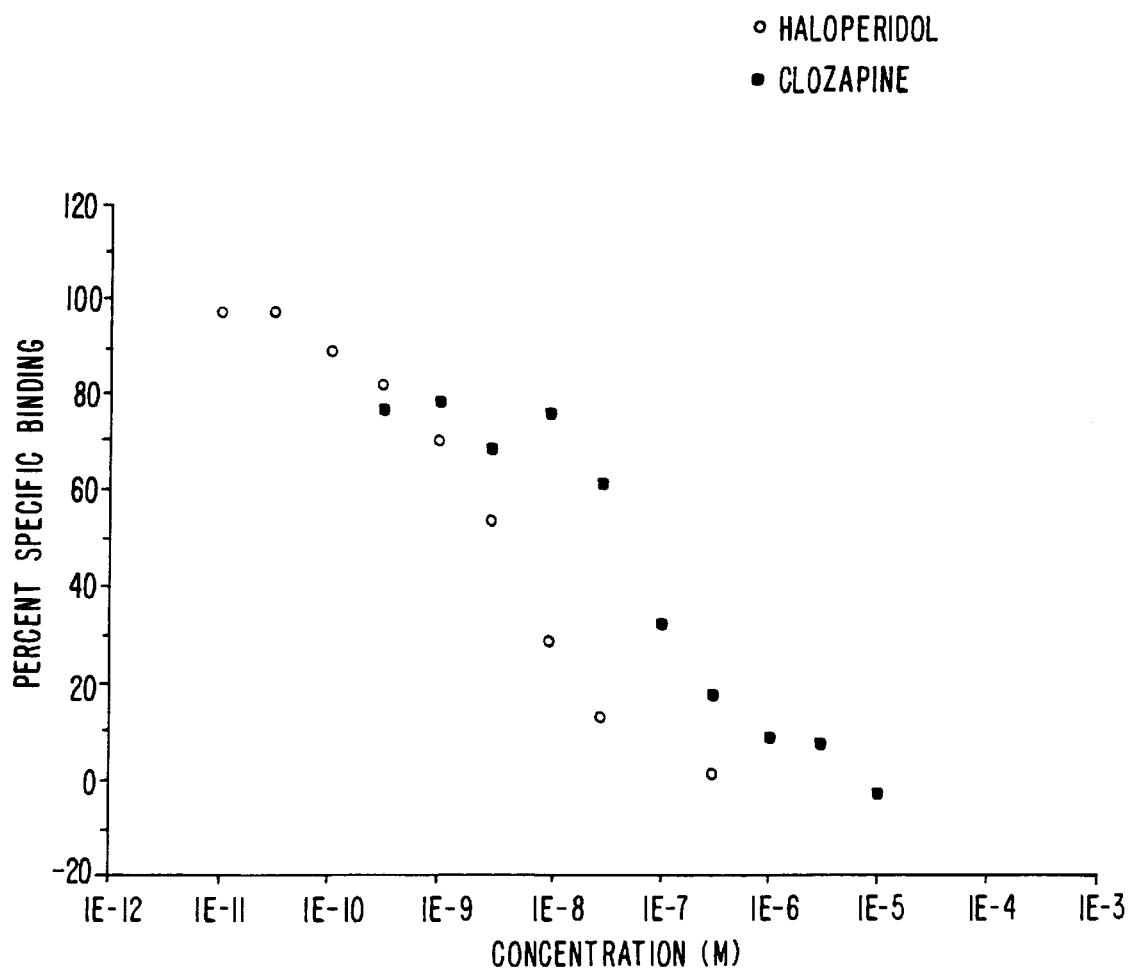
FIG. 13 displays the results of the $IC_{50}/K_i$ determination for clozapine with the dopamine $D_4$ receptor.

The compounds of use in the present invention, being antagonists of dopamine receptor subtypes within the brain, are accordingly of benefit in the treatment and/or prevention of psychotic disorders such as schizophrenia. In particular, the compounds of use in this invention are potent antagonists of the human dopamine $D_4$ receptor subtype. Moreover, the compounds of use in the invention have a selective affinity for the dopamine $D_4$ receptor subtype over other dopamine receptor subtypes, in particular the $D_2$ subtype, and can therefor be expected to manifest fewer side effects than those associated with classical neuroleptic drugs.

The definitions offered below are intended to augment, and not to replace, the art accepted meanings.

The term "independently selected" is used herein to indicate that the groups so described can be identical or different.

The term "alkyl" is used herein to refer to a branched or unbranched, saturated or unsaturated, monovalent hydrocarbon radical having from 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups can be attached to any carbon of the alkyl moiety. Additionally, these groups can be pendent from, or integral to, the alkyl chain.

The term "aryl" is used herein to refer to an aromatic substituent which can be a single aromatic ring or multiple aromatic rings which are fused together, linked covalently, or linked to a common group such as a methylene or ethylene moiety. The common linking group can also be a carbonyl as in benzophenone. The aromatic ring(s) can include phenyl, naphthyl, biphenyl, diphenylmethyl and benzophenone among others.

The term "arylalkyl" is used herein to refer to a subset of "aryl" in which the aryl group is attached to a nucleus as shown in Formulae I–III by a $C_1$–$C_{30}$ alkyl group as defined herein; preferably $C_2$–$C_{20}$ or $C_2$–$C_{18}$ alkyl for $R^7$.

The term "nucleus" is used to refer to a scaffold, backbone or ring structure which is a component of the compounds of the invention. "Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group can also be a carbonyl such as in cyclohexyl phenyl ketone. The term "substituted aryl" encompasses "substituted arylalkyl." "Substituted arylalkyl" defines a subset of "substituted aryl" wherein the substituted aryl group is attached to a nucleus as shown in Formulae I–III by an alkyl group as defined herein.

The term "acyl" is used to describe a ketone substituent, —(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —H.

The term "amino" is used to describe primary amines, R—$NH_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups can be either the same or different and are as described herein for "alkyl groups."

As used herein, the term "acylamino" describes substituents of the general formula RC(O)NR', wherein R' is a lower alkyl group and R represents a nucleus as shown in Formula I–III or an alkyl group, as defined herein, attached to a nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety can be oriented as either a forward or reverse ester (i.e. RC(O)OR' or R'OC(O)R, respectively, wherein R comprises the portion of the ester attached either directly or through an intermediate hydrocarbon chain to a nucleus as shown in Formulae I–III).

As used herein, the term "aryloxy" denotes aromatic groups which are linked to a nucleus as shown in Formulae I–III directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The alkyl group is attached to the nucleus shown in Formula I. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein. R and/or R' can be a nucleus as shown in Formulae I–III.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are substituted by a heteroatom such as nitrogen, oxygen or sulfur. Heteroaryl refers to structures which can be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group can also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to a nucleus as shown in Formula I–III.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "heterocyclicalkyl" defines a subset of "heterocyclic" wherein an alkyl group, as defined herein, links the heterocyclic group to a nucleus as shown in Formulae I–III.

As such, in a first aspect, the present invention provides a compound having a structure according to Formula I:

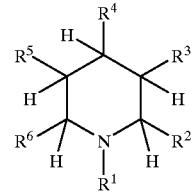

wherein, $R^1$ is a member selected from the group consisting of substituted alkyl, cycloalkyl, aryl, substituted aryl, arylalkyl, substituted arylalkyl, heteroaryl, substituted heteroaryl, heteroarylalkyl and heterocyclicalkyl;

one of $R^2$, $R^3$, $R^4$, $R^5$ and $R^6$ is

and the other four are each hydrogen;

one of X, Y and Z is oxygen and the other two are nitrogen; and $R^7$ is a member selected from the group consisting of $C_4$–$C_{30}$ alkyl, substituted alkyl, cycloalkyl, aryl, substituted aryl, aryl $C_2$–$C_{30}$ alkyl, substituted arylalkyl, heteroaryl, substituted hetereoaryl, heteroarylalkyl, heterocylic and heterocyclic alkyl groups.

Another preferred embodiment of the present invention is a compound having the structure

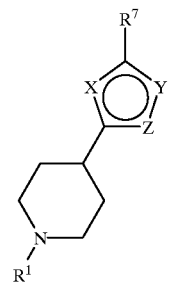

wherein, $R^1$ is a member selected from the group consisting of substituted alkyl, cycloalkyl, aryl, substituted aryl, arylalkyl, arylalkyl, heteroaryl, substituted heteroaryl, heteroarylalkyl, and heterocyclicalkyl;

one of X, Y and Z is oxygen and the other two are nitrogen; and $R^7$ is a member selected from the group consisting of alkyl group consisting of $C_4$–$C_{20}$ alkyl, substituted alkyl, cycloalkyl, aryl, substituted aryl, substituted aryl, $C_2$–$C_{30}$ alkyl, substituted arylalkyl, heteroaryl, substituted heteroaryl, heteroarylalkyl, heterocyclic and heterocyclic alkyl groups.

Another preferred embodiment of the invention is a compound having the structure

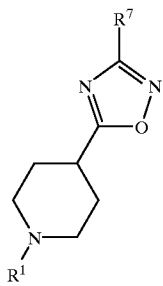

wherein, $R^1$ is a member selected from the group consisting of substituted alkyl, cycloalkyl, aryl, substituted aryl, arylalkyl, substituted arylalkyl, heteroaryl, substituted heteroaryl, heteroarylalkyl, and heterocyclicalkyl;

and further that $R^7$ is a member selected from the group consisting of substituted alkyl, cycloalkyl, aryl, substituted aryl, substituted arylalkyl, heteroaryl, substituted heteroaryl, heteroarylalkyl, heterocyclic and heterocyclic alkyl groups.

A further embodiment of the instant invention is a compound wherein $R^1$ is substituted arylalkyl and $R^7$ is aryl, substituted aryl, heteroaryl or substituted heteroaryl.

In yet another preferred embodiment, the present invention provides compounds having a structure:

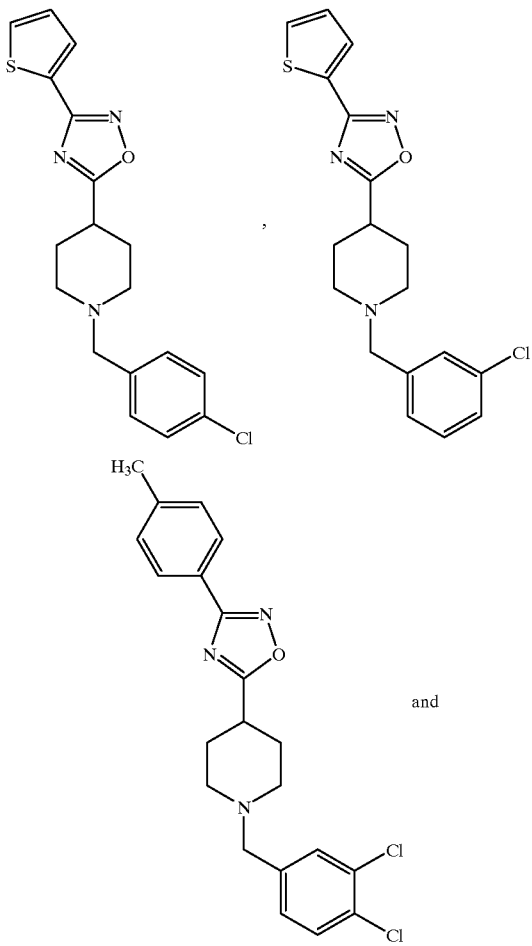

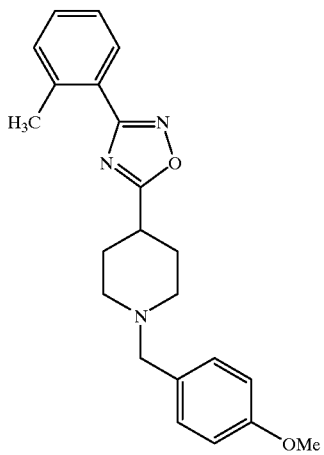

In a presently preferred embodiment, the compounds, or pharmaceutically acceptable salts thereof, are administered in vivo as therapeutic or prophylactic agents. In this embodiment, the invention provides a pharmaceutical composition comprising a compound having a structure according to Formula I combined with a pharmaceutically acceptable carrier or excipient.

For use in medicine, the salts of the compounds of Formula I will be pharmaceutically acceptable salts. Other salts can, however, be useful in the preparation of the compounds according to the invention or of their pharmaceutically acceptable salts. Suitable pharmaceutically acceptable salts of the compounds according to this invention include acid addition salts which can, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, oxalic acid, citric acid, tartaric acid, carbonic acid or phosphoric acid. Furthermore, where the compounds according to the invention carry an acidic moiety, suitable pharmaceutically acceptable salts thereof can include alkali metal salts, e.g. sodium or potassium salts; alkaline earth metal salts, e.g. calcium or magnesium salts; and salts formed with suitable organic ligands, e.g. quaternary ammonium salts.

The term "pharmaceutically acceptable carrier" is intended to include substances capable of being coadministered with the dopamine antagonists of the invention, allowing the antagonist to perform its intended function. Examples of such carriers include solutions, solvents, dispersion media, delay agents, emulsions and the like. The use of such media for pharmaceutically active substances are well known in the art. Any other conventional carrier suitable for use with the dopamine antagonist(s) also fall within the scope of the present invention.

Pharmaceutical compositions for use in accordance with the present invention can also be formulated in conventional manner using one or more physiologically acceptable carriers or excipients as the pharmaceutically acceptable carrier. Thus, the agents and their physiologically acceptable salts and solvates can be formulated for administration by, for example, topical application, injection, inhalation or insufflation (either through the mouth or the nose) or oral, buccal, parenteral or rectal administration.

As such, the agents of the invention can be formulated in a manner appropriate for a specific mode of administration chosen, including, e.g., systemic and topical or localized administration. Techniques and formulations generally can be found in Remmington's Pharmaceutical Sciences, Meade Publishing Co., Easton, Pa. For systemic administration, injection is preferred, including intramuscular, intravenous, intraperitoneal, and subcutaneous. For injection, the agents of the invention can be formulated in liquid solutions, preferably in physiologically compatible buffers such as Hank's solution or Ringer's solution. In addition, the agents can be formulated in solid form and redissolved or suspended immediately prior to use. Lyophilized forms are also included.

For oral administration, the pharmaceutical compositions of the compounds of the invention can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid compositions for oral administration can take the form of, for example, solutions, syrups or suspensions, or they can be presented as a dry product for constitution with water or other suitable vehicle before use. Such liquid compositions can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The compositions can also contain buffer salts, flavoring, coloring and sweetening agents as appropriate. Compositions for oral administration can be suitably formulated to give controlled release of the active modulating agent.

For administration by inhalation, the compositions for use according to the present invention can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the agent and a suitable powder base such as lactose or starch.

The agents can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The agents can also be formulated in rectal compositions such as suppositories or retention enemas, e.g., containing conventional suppository bases such as cocoa butter or other glycerides.

In addition to the formulations described above, the agents can also be formulated as a depot composition. Such long acting formulations can be administered by implantation (for example subcutaneously or intramuscularly) or by intramuscular injection. Thus, for example, the modulating agents can be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents can be used to facilitate permeation. Transmucosal administration can be through nasal sprays or using suppositories. For topical administration, the oligomers of the invention are formulated into ointments, salves, gels, or creams as generally known in the art.

In embodiments in which the agent does not pass rapidly and passively through hydrophobic membranes, injection or inhalation can be more appropriate than ingestion or transdermal delivery. These issues of delivery are related to those for protein-based drugs.

The compositions can, if desired, be provided in a pack or dispenser device, or as a kit with instructions. The composition can contain one or more unit dosage forms containing the active ingredient. The pack can for example comprise metal or plastic foil, such as a blister pack. The pack or dispenser device can be accompanied by instructions for administration, e.g., for use in the methods described herein.

The language "therapeutically effective amount," or "amount effective to treat or prevent" of the compound of the invention is that amount necessary or sufficient to perform its intended function within the subject. The therapeutically effective amount can vary depending on such factors as the type of site being targeted, the type of compound employed, delivery vehicle, mode of administration, the size of the subject, or the severity of the symptom(s). One of ordinary skill in the art can study the aforementioned factors and make the determination regarding the effective amount of the dopamine antagonist without undue experimentation. An in vitro or in vivo assay also can be used to determine an "effective amount" of the dopamine antagonist. The ordinarily skilled artisan would select an appropriate amount of a compound of the invention for use in the aforementioned assay.

The data obtained from cell culture assays, receptor binding assays and animal studies can be used in formulating an appropriate range of dosages for use in subjects. The dosage of such agents lies preferably within a range of circulating or tissue concentrations that include the $ED_{50}$ with little or no toxicity. The dosage can vary within this range depending upon the dosage form employed and the route of administration utilized. For any agent used in the method of the invention, the therapeutically effective dose can be estimated initially from receptor and/or cell culture assays. A dose can be formulated in animal models to achieve a concentration range that includes the $IC_{50}$ (i.e., the concentration of the test modulating agent which achieves a half-maximal inhibition of symptoms). Data from in vitro assays and animal studies can be used to more accurately determine useful doses in humans. Plasma levels of the dopamine antagonists or their metabolites can be measured by numerous means known to those including, but not limited to, immunoassays and high performance liquid chromatography.

The regimen of administration also can affect what constitutes an effective amount. A compound of the invention can be administered alone or in conjunction with other agent(s). Further, several divided dosages, as well as staggered dosages, can be administered daily or sequentially, or the dose can be continuously infused. Further, the dosages of the compounds of the invention can be proportionally increased or decreased as indicated by the exigencies of the therapeutic or prophylactic situation.

When referring to these preformulation compositions as homogeneous, it is meant that the active ingredient is dispersed evenly throughout the composition so that the composition can be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

If desired, the compounds according to this invention can be co-administered with another anti-schizophrenic medicament, for example one producing its effects via $D_2$ and/or $5-HT_2$ receptor blockade. In such circumstances, an enhanced anti-schizophrenic effect can be envisaged without a corresponding increase in side-effects such as those caused by, for example, $D_2$ receptor subtype blockade; or a comparable anti-schizophrenic effect with reduced side-effects can alternatively be envisaged. Such co-administration can be desirable where a patient is already established on an anti-schizophrenic treatment regime involving conventional anti-schizophrenic medicaments such as haloperidol or chlorpromazine.

Thus, in a presently preferred embodiment, a compound of the invention is administered in conjunction with one or more additional compounds having pharmacological activity. Particularly preferred agents are those exhibiting neuroleptic and/or anticholinergic activity. The anticholinergic agent can be a peripheral anticholinergic antagonist selected from the group consisting of N-methylscopolamine, N-methylatropine, propantheline, methantheline, glycopyrrolate and combinations thereof.

The compounds of the invention and pharmaceutical formulations containing the compounds of the invention, as discussed above, can be used as a component of a method for alleviating, treating or preventing a psychotic disorder in a subject. This method comprises administering to said subject an amount of a compound having a structure according to Formula I effective to treat or prevent said psychotic disorder.

In the treatment of schizophrenia, a suitable dosage level is about 0.01 to 250 mg/kg per day, preferably about 0.05 to 100 mg/kg per day, and especially about 0.05 to 5 mg/kg per day. The compounds can be administered on a regimen of 1 to 4 times per day.

In order to alleviate the symptoms of schizophrenia without causing sedation or extrapyramidal side-effects, the dosage level of the compound according to the invention is ideally selected such that the dose administered is effective in substantially completely blocking the dopamine $D_4$ receptor subtype in human brain whilst displaying no or negligible dopamine $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

It is known in the art that agents having neuroleptic properties also exhibit pain relieving properties. For example, Wätjen in EPA 0285032, teaches piperidine derivatives which exhibit neuroleptic as well as pain relieving properties. The determination of an agent's pain relieving properties can be assayed by art-accepted methods such as the acetic acid induced writhing syndrome in mice. See, Siegmund et al., *Proc. Soc. Exp. Biol.* 95:729–731 (1957) and Eckhardt et al., *Proc. Soc. Exp. Biol.* 98:186–188 (1958).

Thus, in a preferred embodiment, the invention provides a compound according to Formula I, which exhibits pain relieving properties. In yet a further preferred embodiment, the invention provides a method for treating or preventing a pain condition. The method comprises administering to a subject, a therapeutically effective amount of a compound according to Formula I.

Suitable dosage ranges and treatment regimens can be ascertained by those of skill in the art without undue experimentation. Methods similar to those discussed above can be utilized to arrive at appropriate quantities and frequencies for administration of the compounds of the invention.

In another preferred embodiment, the invention provides a compound according to Formula I can exhibit a range of diverse biological and pharmacological activities. The compounds can act as agonists or antagonists for receptors such as the muscarinic receptor and the family of dopamine receptors. Further, the compounds can effectively trigger or suppress the characteristic activities and properties of receptors by binding to the receptors or by mechanisms other than direct binding to receptors.

In a preferred embodiment, the invention provides a compound according to Formula I that interacts with a dopamine receptor. In another preferred embodiment, the invention provides a compound which interacts with a dopamine receptor which is a member selected from the group consisting of dopamine $D_2$ receptors, dopamine $D_4$ receptors and combinations thereof.

In a presently preferred interaction is one in which a compound of the invention binds to the receptor. In this embodiment, it is preferred that the compounds according to the present invention have a human dopamine $D_4$ receptor subtype binding affinity ($K_i$) of 100 nM or less, preferably 2 nM or less; and at least a 50-fold, suitably at least a 70-fold, preferably at least a 100-fold, and most preferably at least a 250-fold selective affinity for the $D_4$ subtype relative to the $D_2$ subtype.

In another preferred embodiment, the compounds of the invention are dopamine receptor antagonists. In another preferred embodiment, the compounds of the invention act as antagonists towards a dopamine receptor which is a member selected from the group consisting of dopamine $D_2$ receptors, dopamine $D_4$ receptors and combinations thereof. In these embodiments, the antagonist activity can arise from a direct binding of a compound of Formula I to a dopamine receptor or, alternatively, through another mechanism which induces the characteristics of dopamine receptor antagonism.

The compounds of the invention are useful as pharmaceutical agents and as probes for assaying the biological activity of both the compounds of the invention and structurally analogous compounds. The compounds of the invention can also be used as probes to assay the binding or activity of compounds which behave in a functionally analogous way (e.g., neuroleptics, dopamine receptor antagonists, etc.). Further, the compounds are useful as intermediates for further synthetic elaboration.

The compounds in accordance with the present invention can be prepared by a wide range of processes that can be selected by those skilled in the art. A representative synthetic process is set forth in FIG. 1. Protection of the commercially available isonipecotic acid with di-tert-butyl dicarbonate in the presence of NaOH in water/dioxane (1:1) provided N-Boc-isonipecotic acid 1. Treatment of nitriles with hydroxylamine hydrochloride gave the amide oxides 2. The protected 1,2,4-oxadiazoles 3 were generated via condensation of the amide oxides 2 and the carboxylic acid 1 in the presence of 1-(3-dimethylaminopropyl)-3-ethylcarboduimide hydrochloride (EDCI) followed by heating at 50° C. for 14 hours and then 110° C. for 3 hours. Deprotection of 3 was accomplished by treatment with hydrogen chloride in dioxane at room temperature to supply hydrochloride salt of the secondary amine 4. Finally, condensation of the secondary amines 4 with commercial alkyl halides in the presence of diisopropyl ethylamine yielded the 4-(1,2,4-oxadiazolyl)piperidines 5.

Where they are not commercially available, the starting materials of Formulae I–III and their substructures discussed above, can be prepared by procedures analogous to those described in the accompanying Examples, or by standard methods well-known from the art. It will be appreciated that any compound of Formulae I–III initially obtained from any of the above processes can, where appropriate, subsequently be elaborated into a further desired compound using techniques known from the art.

When processes for the preparation of the compounds according to the invention give rise to mixtures of isomers, these isomers can be separated by conventional techniques such as preparative chromatography. When enantiomeric compounds are produced, the compounds can be prepared in racemic form, or individual enantiomers can be prepared either by enantiospecific synthesis or by resolution. The compounds can, for example, be resolved into their component enantiomers by standard techniques such as preparative HPLC (e.g., using a Pirkle column), or the formation of diastereomeric pairs by salt formation with an optically active acid, such as (−)-di-p-toluoyl-D-tartaric acid and/or (+)-di-p-toluoyl-L-tartaric acid, followed by fractional crystallization and regeneration of the free base. The compounds can also be resolved by formation of diastereomeric esters or amides, followed by chromatographic separation and removal of the chiral auxiliary.

During any of the above synthetic sequences it can be necessary and/or desirable to protect sensitive or reactive groups on any of the molecules concerned. This can be achieved by means of conventional protecting groups, such as those described in *Protective Groups in Organic Chemistry*, ed. J. F. W. McOmie, Plenum Press, 1973;and T. W. Greene & P. G. M. Wuts, *Protective Groups in Organic Synthesis*, John Wiley & Sons, 1991. The protecting groups can be removed at a convenient subsequent stage using methods known from the art.

In yet another preferred embodiment, the compound of the invention is radiolabeled with a radionuclide such as $^3$H, $^{14}$C, $^{125}$I or the like. Thus, within the scope of the invention are compounds according to Formula I, in which one or more atoms is replaced with a radionuclide.

The compounds can be assayed for their binding affinity to dopamine receptors by methods recognized in the art. Assays are known for the binding of ligands to the $D_2$ receptor, see, for example, Jarvis et al., *J. Receptor Res.* 13: 573–590 (1993); Gundlach et al., *Life Sciences* 35: 1981–1988 (1984) and the $D_4$ receptor; see, for example, Van Tol et al., *Nature* 358: 149 (1992); Van Tol et al., *Nature* 350: 610 (1991); Seeman et al., *Eur. J Pharm.* 233: 173 (1993). These methods can be utilized as disclosed or they can be modified as needed. Suitable modifications will be apparent to those of skill in the art and can be practiced without undue experimentation.

The following Examples illustrate the preparation of compounds according to the invention.

EXAMPLES

The following examples are offered to illustrate, but not to limit the claimed invention.

Example 1 illustrates the synthesis of an amine protected piperidine derivative, N-Boc-isonipecotic acid.

Example 2 illustrates the synthesis of three oxime intermediates which are useful in synthesizing the compounds of the invention.

Example 3 illustrates the synthesis of the amine protected adducts between the oxime intermediates of Example 2 and N-Boc-isonipecotic acid.

Example 4 illustrates the acidic deprotection of the piperidine nitrogen.

Example 5 illustrates the functionalization of the piperidine nitrogen.

Example 6 illustrates one type of assay which is useful for determining the binding affinity for the dopamine D2 and D4 receptors exhibited by compounds of the invention.

Example 1

This Example illustrates the synthesis of an amine protected piperidine derivative, N-Boc-isonipecotic acid.

1.1 Materials and Methods

The following materials and methods were used throughout the following synthetic procedures. All reagents were purchased from Aldrich, Fischer, Fluka and Merck and all were used without further purification. All solvents were HPLC grade and were used as supplied.

H NMR spectra were recorded using Bruker AM (500 MHz) in the deuterated solvent as indicated. TLC analyses were performed on Merck (Kieselgel 60F-254) silica gel plates and visualized by detection with UV light (220 nm or 254 nm) or ninhydrin indicator. Flash-column chromatography was performed on cartridges from Biotage (silica-gel, 40–60 uM). Both purity analyses and preparative purifications were performed using a Shimadzu LC-8A binary high pressure gradient system (Shimadzu) controlled through the PE SCIEX sample control software. A Gilson 215 autosampler was incorporated into the system. Shimadzu SPD-10A dual wavelength detectors were used to acquire UV spectra. Analytical HPLC separations were made using a 4.6 mm i.d.×5 cm $C_{18}$ YMC column. Large scale preparative HPLC-MS 35 separations were carried out using a 20 mm i.d.×5 cm $C_{18}$ YMC column at a flow rate of 35 mL per minute. For LC-MS using analytical-scale HPLC, all spectra were recorded using a PE SCIEX 150EX single quadropole mass spectrometer equipped with an API (electrospray) ion source. Buffer A was aqueous 0.05% trifluoroacetic acid (TFA) and buffer B was 0.035% TFA in acetonitrile (v/v). The gradient used in analytical and preparative HPLC was an initial hold of 10% buffer B for one minute. Following the initial hold the compounds were separated on the $C_{18}$ column using a gradient of 10% to 90% buffer B in 4.5 minutes in analytical mode and the same gradient over 10 minutes in preparative mode.

The following examples, Examples 1–5, describe the preparation of compounds represented in the schematic process of FIG. 1.

1.2 Synthesis of N-Boc-isonipecotic acid (1)

To a solution of isonipecotic acid (15 g, 117.2 mmol) in 40 mL dioxane and 40 mL 1M NaOH was added di-tert-butyl dicarbonate (28.14 g, 129 mmol). The mixture was allowed to stir at room temperature. After 12 hours the mixture was then partitioned between diethyl ether and water. The aqueous phase was acidified to pH 3.0 with 1N HCl and extracted with ethyl acetate (4×100 mL). The organic phases were washed with brine, dried ($MgSO_4$) and concentrated to give a white solid (22.96 g, 85%); m/z $(M+H)^+230.2$ ($C_{11}H_{19}NO_4$).

Example 2

This Example illustrates the synthesis of three oxime intermediates which are useful in synthesizing the compounds of the invention.

2.1 Synthesis of p-Tolylamidoxime (2a)

Hydroxylamine hydrochloride (1.3 g, 18 mmol) was added to a solution of $Et_3N$ (2.5 mL, 18 mmol) in 50% aqueous EtOH (4.2 mL). After 30 minutes p-methylbenzonitrile (1.7 g, 15 mmol) in EtOH (40 mL) was added and the mixture was allowed to reflux for 8 hours. The mixture was cooled to room temperature and poured into water (100 mL). The aqueous solution was decanted, concentrated to half of its original volume. Upon standing the product crystallized to afford 2a as a white solid (1.7 g, 62 %); m/z $(M+H)^+150.2$ ($C_8H_{10}N_2O$).

2.2 Synthesis of Thienylamidoxime (2b).

Compound 2b was synthesized utilizing a procedure analogous to that set forth in 2.1, above. Yield: 90 %. m/z $(M+H)^+143.2$ ($C_5H_6N_2OS$).

2.3 Synthesis of o-Tolylamidoxime (2c).

Compound 2c was synthesized utilizing a procedure analogous to that set forth in 2.1. Yield: 90 %. m/z $(M+H)^+$ 150.2 ($C_8H_{10}N_2O$).

Example 3

This Example illustrates the synthesis of the amine protected adducts between the oxime intermediates of Example 2 and N-Boc-isonipecotic acid.

3.1 Synthesis 4-(3-p-tolyl-1,2,4-oxadiazol-5-yl)N-Boc piperidine (3a)

To 1 (1 g, 5 mmol) in dioxane (15 mL) was added 1-(3-dimethylaminopropyl)-3-ethylcarbodiimide hydrochloride (0.84 g, 4.4 mmol) and 2a (0.85 g, 4.6 mmol). The mixture was allowed to stir at 50° C. for 14 hours and then heated to 110° C. for 3 hours. After removal of the solvent under vacuum, the reaction mixture was purified by flash-chromatography on a silica gel column eluting with 20% ethyl acetate in hexane. Concentration of the appropriate fractions gave 3a as crystals (650 mg, 42%); m/z $(M+H)^+$ 342.2 ($C_{19}H_{24}N_3O_3$).

3.2 Synthesis of 4-[3-(2-thienyl)-1,2,4-oxadiazol-5-yl]-N-Boc piperidine (3b).

Compound 3b was synthesized utilizing a procedure analogous to that set forth in 3.1, above. Yield: 90%. m/z $(M+H)^+336.1$ ($C_{16}H_{21}N_3O_3S$).

3.3 Synthesis of 4-(3-o-tolyl-1,2,4-oxadiazol-5-yl)N-Boc piperidine (3c)

Compound 3b was synthesized utilizing a procedure analogous to that set forth in 3.1, above. Yield: quantitative. m/z $(M+H)^+343.2$ ($C_{19}H_{25}N_3O_3$).

Example 4

This Example illustrates the acidic deprotection of the piperidine nitrogen.

4.1 Synthesis of 4-(3-p-tolyl-1,2,4-oxadiazol-5-yl) piperidine hydrochloride (4a).

Compound 3a (500 mg) was treated with a solution of 4M HCl in dioxane for 1 hour. The solvent was removed under vacuum to give HCl salt of the title compound (376 mg, 92%); m/z $(M+H)^+242.1$ ($C_{14}H_{16}N_3O$).

4.2 Synthesis of 4-[3-(2-thienyl)-1,2,4-oxadiazol-5-yl] piperidine hydrochloride (4b).

Compound 4b was synthesized utilizing a procedure analogous to that set forth in 4.1, above. Yield: quantitative. m/z $(M+H)^+236.3$ ($C_{11}H_{13}N_3OS$).

4.3 Synthesis of 4-(3-o-tolyl-1,2,4-oxadiazol-5-yl) piperidine hydrochloride (4c).

Compound 4c was synthesized utilizing a procedure analogous to that set forth in 4.1, above. Yield: quantitative. m/z $(M+H)^+243.2$ ($C_{14}H_{17}N_3O$).

Example 5

This Example illustrates the functionalization of the piperidine nitrogen.

5.1 Synthesis of 4-(3-p-tolyl-1,2,4-oxadiazol-5-yl)-N-(3,4-dichlorobenzyl) piperidine (5a).

To 4a (28 mg, 0.1 mmol, 1.0 eq) in DMF (0.5 mL) and $EtNiPr_2$ (35 µL, 0.2 mmol), was added 3,4-dichlorobenzyl chloride (14 µL, 0.1 mmol). The mixture was allowed to stir at 55° C. for 12 hours. The crude is directly purified by HPLC (10–100% $H_2O$/acetonitrile) to afford the desired compound (35 mg, 87%); m/z $(M+H)^+402.1$ ($C_{21}H_{21}Cl_2N_3O$); 500 MHZ, $^1H$ NMR ($CD_3OD$): 2.2 (m, $^1H$, H-4), 2.40 (s, 3H, $CH_3$), 2.46 (m, 2H), 3.26 (m, 2H), 3.5 (m, 2H), 3.65 (m, 2H), 4.40 (s, 2H, $CH_2$—Ar), 7.32–7.92 (m, 7H).

5.2 Synthesis of 4-[3-(2-thienyl)-1,2,4-oxadiazol-5-yl]-N-(4-chlorobenzyl) piperidine (5b).

Compound 5b was synthesized utilizing a procedure analogous to that set forth in 5.1, above. Yield: 27%. m/z $(M+H)^+359.1$ ($C_{18}H_{18}CN_3OS$). 500 MHz $^1H$ NMR ($CD_3OD$) (m, 1H, H-4), 2.46 (m, 2H), 3.24 (m, 2H), 3.45 (m, 2H), 3.64 (m, 2H), 4.39 (s, 2H, $CH_2$—Ar), 7.30 (m, 1H), 7.51–7.59 (m, 4H), 7.68 (d, 1H, J=4.85 Hz), 7.78 (d, 1H, J=3.2 Hz).

5.3 Synthesis of 4-[3-(2-thienyl)-1,2,4-oxadiazol-5-yl]-N-(3-chlorobenzyl) piperidine (5c).

Compound 5c was synthesized utilizing a procedure analogous to that set forth in 5.1, above. Yield: 26%. m/z $(M+H)^+359-1$ ($C_{18}H_{18}CN_3OS$). 500 MHz $^1H$ NMR ($CD_3OD$): 2.22 (m, 1H, H-4), 2.47 (m, 2H), 3.28 (m, 2H), 3.47 (m, 2H), 3.64 (m, 2H), 4.41 (s,2H, $CH_2$—Ar), 7.19 (m, 1H), 7.47–7.77 (m, 6H).

5.4 Synthesis of 4-(3-o-tolyl-1,2,4-oxadiazol-5-yl)-N-(4-methoxybenzyl) piperidine (5d).

Compound 5d was synthesized utilizing a procedure analogous to that set forth in 5.1, above. Yield: 22%. m/z $(M+H)^+363.2$ ($C_{22}H_{25}N_3O_2$). 500 MHz $^1H$ NMR ($CD_3OD$): 2.20 (m, 1H, H-4), 2.47 (m, 2H), 2.56 (s, 3H, $CH_3$), 3.22 (m, 2H), 3.45 (m, 2H), 3.46 (m, 2H), 3.66 (m, 2H), 3.82 (s, 3H, $OCH_3$), 4.33 (s, 2H, $CH_2$—Ar), 7.02–7.92 (m, 4H).

Example 6

This Example illustrates one useful assay for determining the binding affinity for the dopamine $D_2$ and $D_4$ receptors exhibited by compounds of the invention.

6.1 Materials and Methods

6.1a Assay Conditions

The assays were performed using the following methods:

| Receptor | Tissue | reference compound | reference |
|---|---|---|---|
| $D_2$(h) | Human recombinant (A9L cells) | (+)butaclamol | Grandy et al. (1989) |
| $D_{4.4}$(h) | Human recombinant (CHO cells) | Clozapine | Van Tol et al. (1992) |

Experimental Conditions

| receptor | Ligand | concentration | Nonspecific | incubation |
|---|---|---|---|---|
| $D_2$(h) | [$^3$H]spiperone | 0.2 nM | (+)butaclamol (10 μM) | 60 min/22° C. |
| $D_{4.4}$(h) | [$^3$H]spiperone | 0.5 nM | (+)butaclamol (10 μM) | 60 min/22° C. |

Following incubation, the membranes were rapidly filtered under vacuum through GF/B glass fiber filters (Packard). The filters were then washed several times with an ice-cold buffer using a Packard cell harvester.

Bound radioactivity was measured with a scintillation counter (Topcount, Packard) using a liquid scintillation cocktail (Microscint 0, Packard).

6.1b. Experimental protocols

The compounds were tested in each assay at ten concentrations in duplicate to obtain competition curves.

In each experiment, the respective reference compound was simultaneously tested at eight concentrations in duplicate to obtain competition curves in order to validate this experiment.

6.1c. Data handling

The specific radioligand binding to the receptors is defined as the difference between total binding and nonspecific binding determined in the presence of an excess of unlabelled ligand (see section 2.1).

Results are expressed as a percent of control specific binding obtained in the presence of the test compounds.

$IC_{50}$ values (concentration required to inhibit 50% of specific binding) and Hill coefficients (nH) were determined for the test compounds and the reference compounds by non-linear regression analysis of their competition curves. These parameters were obtained by Hill equation curve fitting. The inhibition constants ($K_i$) were calculated from the Cheng Prusoff equation ($K_i=IC_{50}/(1+L/K_D)$, where L=concentration of radioligand in the assay, and KD=affinity of radioligand for the receptor).

6.1d Incubation Conditions

Reactions were carried out in 50 mM TRIS-HCl (pH 7.4) containing 120 mM NaCl, 5 mM KCl, 5 mM $MgCl_2$, 1mM EDTA for 60 minutes at 25° C. The reaction was terminated by rapid vacuum filtration onto glass fiber filters. Radioactivity trapped onto the filters was determined and compared to control values in order to ascertain any interactions of test compound(s) with the cloned dopamine $D_2$ short binding site.

6.2 Results

The results of the dopamine $D_2$ and $D_4$ receptor assays are displayed in Tables 1 through 12, below. Graphic display of the results is found in FIGS. 2 through 13.

Table 1 displays the % inhibition and % specific binding of compound 5a to the dopamine $D_2$ receptor. A graphic representation of the percent specific binding versus the concentration of compound 5a is displayed in FIG. 2.

TABLE 1

| Receptor Concentration NEUROTRANSMITTER RELATED Dopamine, $D_2$ (Human Recombinant)* | % Inhibition | (Average; N = 2) % Specific Binding |
|---|---|---|
| 3.0E-10 | 10.14% | 89.86% |
| 1.0E-9 | 6.60% | 93.40% |
| 3.0E-9 | 9.24% | 90.76% |
| 1.0E-8 | 10.30% | 89.70% |
| 3.0E-8 | −7.32% | 107.32% |
| 1.0E-7 | 15.26% | 84.74% |
| 3.0E-7 | −0.92% | 100.92% |
| 1.0E-6 | −2.71% | 102.17% |
| 3.0E-6 | 0.63% | 99.37% |
| 1.0E-5 | −15.54% | 115.54% |

Table 2 displays the % inhibition and % specific binding of compound 5a to the dopamine $D_4$ receptor. A graphic representation of the percent specific binding versus the concentration of compound 5a is displayed in FIG. 3.

TABLE 2

| Receptor Concentration NEUROTRANSMITTER RELATED Dopamine, D4.4 (Human Recombinant)* | % Inhibition | (Average; N = 2) % Specific Binding |
|---|---|---|
| 3.0E-10 | 9.11% | 90.89% |
| 1.0E-9 | 19.85% | 80.15% |
| 3.0E-9 | 15.56% | 84.44% |
| 1.0E-8 | 18.95% | 81.05% |
| 3.0E-8 | 23.72% | 76.28% |
| 1.0E-7 | 23.15% | 76.85% |
| 3.0E-7 | 19.59% | 80.41% |
| 1.0E-6 | 53.44% | 46.56% |
| 3.0E-6 | 83.62% | 16.38% |
| 1.0E-5 | 96.43% | 3.57% |

Table 3 displays the % inhibition and % specific binding of compound 5b to the dopamine $D_2$ receptor. A graphic representation of the percent specific binding versus the concentration of compound 5b is displayed in FIG. 4.

TABLE 3

| Receptor Concentration NEUROTRANSMITTER RELATED Dopamine, D2s (Human Recombinant)* | % Inhibition | (Average; N = 2) % Specific Binding |
|---|---|---|
| 3.0E-10 | −16.22% | 116.22% |
| 1.0E-9 | −3.88% | 103.88% |
| 3.0E-9 | 2.71% | 97.29% |
| 1.0E-8 | −2.89% | 102.89% |
| 3.0E-8 | −4.19% | 104.19% |
| 1.0E-7 | −12.21% | 112.21% |
| 3.0E-7 | −16.50% | 116.50% |
| 1.0E-6 | 8.70% | 91.30% |
| 3.0E-6 | 38.06% | 61.94% |
| 1.0E-5 | 75.39% | 24.61% |

Table 4 displays the % inhibition and % specific binding of compound 5b to the dopamine $D_4$ receptor. A graphic representation of the percent specific binding versus the concentration of compound 5b is displayed in FIG. 5.

TABLE 4

| Receptor Concentration<br>NEUROTRANSMITTER RELATED<br>Dopamine, D4.4 (Human Recombinant)* | % Inhibition | (Average; N = 2)<br>% Specific<br>Binding |
|---|---|---|
| 3.0E-10 | 17.71% | 82.29% |
| 1.0E-9 | 24.01% | 75.99% |
| 3.0E-9 | 26.92% | 73.08% |
| 1.0E-8 | 46.39% | 53.61% |
| 3.0E-8 | 70.34% | 29.66% |
| 1.0E-7 | 77.21% | 22.79% |
| 3.0E-7 | 95.72% | 4.28% |
| 1.0E-6 | 99.56% | 0.44% |
| 3.0E-6 | 100.19% | -0.19% |
| 1.0E-5 | 103.87% | -3.8% |

Table 5 displays the % inhibition and % specific binding of compound 5c to the dopamine $D_2$ receptor. A graphic representation of the percent specific binding versus the concentration of compound 5c is displayed in FIG. 6.

TABLE 5

| Receptor Concentration<br>NEUROTRANSMITTER RELATED<br>Dopamine, D2s (Human Recombinant)* | % Inhibition | (Average; N = 2)<br>% Specific<br>Binding |
|---|---|---|
| 3.0E-10 | 1.46% | 98.54% |
| 1.0E-9 | 5.18% | 94.82% |
| 3.0E-9 | -8.31% | 108.13% |
| 1.0E-8 | 11.65% | 88.35% |
| 3.0E-8 | 15.08% | 84.92% |
| 1.0E-7 | 12.29% | 87.71% |
| 3.0E-7 | 5.44% | 94.56% |
| 1.0E-6 | -0.72% | 100.72% |
| 3.0E-6 | -2.17% | 102.17% |
| 1.0E-5 | 67.05% | 32.95% |

Table 6 displays the % inhibition and % specific binding of compound 5c to the dopamine $D_4$ receptor. A graphic representation of the percent specific binding versus the concentration of compound 5c is displayed in FIG. 7.

TABLE 6

| Receptor Concentration<br>NEUROTRANSMITTER RELATED<br>Dopamine, D4.4 (Human Recombinant)* | % Inhibition | (Average; N = 2)<br>% Specific<br>Binding |
|---|---|---|
| 3.0E-10 | -8.59% | 108.59% |
| 1.0E-9 | -6.58% | 106.58% |
| 3.0E-9 | 4.85% | 95.15% |
| 1.0E-8 | 18.08% | 81.92% |
| 3.0E-8 | 40.01% | 59.99% |
| 1.0E-7 | 70.84% | 29.16% |
| 3.0E-7 | 95.21% | 4.79% |
| 1.0E-6 | 98.26% | 1.74% |
| 3.0E-6 | 95.40% | 4.60% |
| 1.0E-5 | 107.32% | -7.32% |

Table 7 displays the % inhibition and % specific binding of compound 5d to the dopamine $D_2$ receptor. A graphic representation of the percent specific binding versus the concentration of compound 5d is displayed in FIG. 8.

TABLE 7

| Receptor Concentration<br>NEUROTRANSMITTER RELATED<br>Dopamine, D2s (Human Recombinant)* | % Inhibition | (Average; N = 2)<br>% Specific<br>Binding |
|---|---|---|
| 3.0E-10 | 14.81% | 85.19% |
| 1.0E-9 | -3.77% | 103.77% |
| 3.0E-9 | -4.70% | 104.70% |
| 1.0E-8 | 0.02% | 99.98% |
| 3.0E-8 | 0.19% | 99.81% |
| 1.0E-7 | -4.63% | 104.63% |
| 3.0E-7 | -17.16% | 117.16% |
| 1.0E-6 | -6.21% | 106.21% |
| 3.0E-6 | -13.13% | 113.13% |
| 1.0E-5 | 60.46% | 39.54% |

Table 8 displays the % inhibition and % specific binding of compound 5d to the dopamine $D_4$ receptor. A graphic representation of the percent specific binding versus the concentration of compound 5d is displayed in FIG. 9.

TABLE 8

| Receptor Concentration<br>NEUROTRANSMITTER RELATED<br>Dopamine, D4.4 (Human Recombinant)* | % Inhibition | (Average; N = 2)<br>% Specific<br>Binding |
|---|---|---|
| 3.0E-10 | -0.93% | 100.93% |
| 1.0E-9 | -2.00% | 102.00% |
| 3.0E-9 | 3.59% | 96.41% |
| 1.0E-8 | 7.92% | 92.08% |
| 3.0E-8 | 22.94% | 77.06% |
| 1.0E-7 | 52.54% | 47.46% |
| 3.0E-7 | 77.10% | 22.90% |
| 1.0E-6 | 93.42% | 6.58% |
| 3.0E-6 | 87.82% | 12.18% |
| 1.0E-5 | 97.85% | 2.15% |

Table 9 displays the % inhibition and % specific binding of haloperidol to the dopamine $D_2$ receptor. A graphic representation of the percent specific binding versus the concentration of haloperidol is displayed in FIG. 10. This experiment was run as a blind validation of the assay method.

TABLE 9

| Receptor Concentration<br>NEUROTRANSMITTER RELATED<br>Dopamine, D2s (Human Recombinant)* | % Inhibition | (Average; N = 2)<br>% Specific<br>Binding |
|---|---|---|
| 3.0E-10 | 17.25% | 82.75% |
| 1.0E-9 | 29.64% | 70.36% |
| 3.0E-9 | 49.83% | 50.17% |
| 1.0E-8 | 71.09% | 28.91% |
| 3.0E-8 | 85.13% | 14.87% |
| 1.0E-7 | 97.01% | 2.99% |
| 3.0E-7 | 98.52% | 1.48% |
| 1.0E-6 | 96.36% | 3.64% |
| 3.0E-6 | 100.18% | -0.18% |
| 1.0E-5 | 98.75% | 1.25% |

Table 10 displays the % inhibition and % specific binding of haloperidol to the dopamine $D_4$ receptor. A graphic representation of the percent specific binding versus the concentration of haloperidol is displayed in FIG. 11. This experiment was run as a blind validation of the assay method.

TABLE 10

| Receptor Concentration NEUROTRANSMITTER RELATED Dopamine, D4.4 (Human Recombinant)* | % Inhibition | (Average; N = 2) % Specific Binding |
|---|---|---|
| 3.0E-10 | 24.98% | 75.02% |
| 1.0E-9 | 27.34% | 72.66% |
| 3.0E-9 | 43.44% | 56.56% |
| 1.0E-8 | 61.24% | 38.76% |
| 3.0E-8 | 83.15% | 16.85% |
| 1.0E-7 | 90.55% | 9.45% |
| 3.0E-7 | 93.02% | 6.98% |
| 1.0E-6 | 90.99% | 9.01% |
| 3.0E-6 | 102.35% | -2.35% |
| 1.0E-5 | 99.44% | 0.56% |

Table 11 displays the % inhibition and % specific binding of clozapine to the dopamine $D_2$ receptor. A graphic representation of the percent specific binding versus the concentration of clozapine is displayed in FIG. 12. This experiment was run as a blind validation of the assay method.

TABLE 11

| Receptor Concentration NEUROTRANSMITTER RELATED Dopamine, D2s (Human Recombinant)* | % Inhibition | (Average; N = 2) % Specific Binding |
|---|---|---|
| 3.0E-10 | 1.29% | 98.71% |
| 1.0E-9 | 10.75% | 89.25% |
| 3.0E-9 | 35.72% | 64.28% |
| 1.0E-8 | 9.15% | 90.85% |
| 3.0E-8 | 13.25% | 86.75% |
| 1.0E-7 | 23.11% | 76.89% |
| 3.0E-7 | 40.06% | 59.94% |
| 1.0E-6 | 79.55% | 20.45% |
| 3.0E-6 | 93.48% | 6.52% |
| 1.0E-5 | 97.20% | 2.80% |

Table 12 displays the % inhibition and % specific binding of clozapine to the dopamine $D_4$ receptor. A graphic representation of the percent specific binding versus the concentration of clozapine is displayed in FIG. 13. This experiment was run as a blind validation of the assay method.

TABLE 12

| Receptor Concentration NEUROTRANSMITTER RELATED Dopamine, D4.4 (Human Recombinant)* | % Inhibition | (Average; N = 2) % Specific Binding |
|---|---|---|
| 3.0E-10 | 21.79% | 78.21% |
| 1.0E-9 | 20.19% | 79.81% |
| 3.0E-9 | 30.21% | 69.79% |
| 1.0E-8 | 22.82% | 77.18% |
| 3.0E-8 | 37.18% | 62.82% |
| 1.0E-7 | 66.60% | 33.40% |
| 3.0E-7 | 81.72% | 18.28% |
| 1.0E-6 | 90.78% | 9.22% |
| 3.0E-6 | 92.04% | 7.96% |
| 1.0E-5 | 102.47% | -2.47% |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to Formula I:

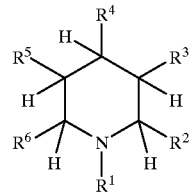

wherein, $R^1$ is a member selected from the group consisting of cycloalkyl, aryl, substituted aryl, arylalkyl, substituted arylalkyl, heteroaryl, substituted heteroaryl, heteroarylalkyl and heterocyclicalkyl;

one of $R^2$, $R^3$, $R^4$, $R^5$ and $R^6$ is

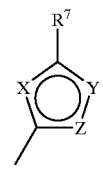

and the other four are each hydrogen;

one of X, Y and Z is oxygen and the other two are nitrogen;

$R^7$ is a member selected from the group consisting of $C_4$–$C_{30}$ alkyl, cycloalkyl, aryl, heteroaryl, substituted hetereoaryl, heteroarylalkyl, heterocyclic and heterocyclic alkyl groups.

2. A compound having the structure

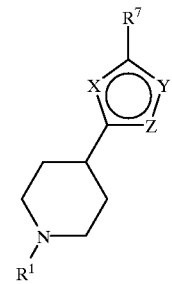

wherein, $R^1$ is a member selected from the group consisting of cycloalkyl, aryl, substituted aryl, arylalkyl, substituted arylalkyl, heteroaryl, substituted heteroaryl, heteroarylalkyl and heterocyclicalkyl;

one of X, Y and Z is oxygen and the other two are nitrogen; and $R^7$ is a member selected from the group consisting of $C_2$–$C_{30}$ alkyl groups, cycloalkyl, aryl, heteroaryl, substituted hetereoaryl, heteroarylalkyl, heterocyclic and heterocyclic alkyl groups.

3. A compound having the structure

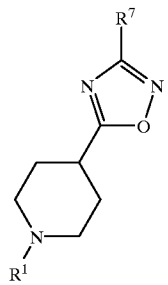

wherein $R^1$ is a member selected from the group consisting of cycloalkyl, aryl, substituted aryl, arylalkyl, substituted arylalkyl, substituted arylalkyl, heteroaryl, substituted heteroaryl, heteroarylalkyl and heterocyclicalkyl; and $R^7$ is a member selected from the group consisting of substituted alkyl, cycloalkyl, aryl, heteroaryl, substituted heteroaryl, heteroarylalkyl, heterocyclic and heterocyclic alkyl groups.

4. A compound of claim 3 wherein $R^1$ is substituted arylalkyl and $R^7$ is aryl, heteroaryl or substituted heteroaryl.

5. The compound of claim 4 selected from the group consisting of:
   4-(3-p-tolyl-1,2,4-oxadiazol-5-yl)-N-(3-,4-dichlorobenzyne)piperidine,
   4-[3-(2-thienyl)-1,2,4-oxadiazol-5-yl]-N-(4-chlorobenzyl)piperidine,
   4-[3-(2-thienyl)-1,2,4-oxadiazol-5yl]-N-(3-chlorobenzyl)piperidine, and
   4-(3-o-tolyl-1,2,4-oxadiazol-5-yl)-N-(4-methoxybenzyl)piperidine.

6. A pharmaceutical composition comprising a compound according to claim 1 and a pharmaceutically acceptable carrier.

7. The pharmaceutical composition according to claim 6 further comprising a compound which is a member selected from the group consisting of neuroleptic agents and anticholinergic agents.

8. The pharmaceutical composition of claim 7 in which said anticholinergic agent is a peripheral anticholinergic antagonist selected from the group consisting of N-methylscopolamine, N-methylatropine, propantheline, methantheline, glycopyrrolate and combinations thereof.

9. A method of alleviating or treating a psychotic disorder in a subject comprising:
   administering to said subject an amount of a compound according to claim 1 effective to treat said psychotic disorder.

10. The method according to claim 9, wherein said amount is from about 0.01 mg/kg per day to about 250 mg/kg per day.

11. The method according to claim 10, wherein said amount is from about 0.05 mg/kg per day to about 100 mg/kg per day.

12. The method according to claim 11, wherein said amount is from about 0.05 mg/kg per day to about 5 mg/kg per day.

13. A method for alleviating, treating or preventing pain in a subject comprising:
   administering to said subject an amount of a compound according to claim 1 effective to treat or prevent said pain.

14. The method according to claim 13, wherein said amount is from about 0.01 mg/kg per day to about 250 mg/kg per day.

15. The method according to claim 14, wherein said amount is from about 0.05 mg/kg per day to about 100 mg/kg per day.

16. The method according to claim 15, wherein said amount is from about 0.05 mg/kg per day to about 5 mg/kg per day.

17. A compound according to claim 1, in which one or more atoms is replaced with a radionuclide.

* * * * *